US010075636B2

(12) United States Patent
Wan et al.

(10) Patent No.: US 10,075,636 B2
(45) Date of Patent: Sep. 11, 2018

(54) ULTRA-SMALL CAMERA MODULE WITH WIDE FIELD OF VIEW, AND ASSOCIATE LENS SYSTEMS AND METHODS

(71) Applicant: OmniVision Technologies, Inc., Santa Clara, CA (US)

(72) Inventors: Tsung Wei Wan, Hsinchu (TW); Ting-Yu Cheng, New Taipei (TW); Wei-Ping Chen, New Taipei (TW); Chuen-Yi Yin, New Taipei (TW)

(73) Assignee: OmniVision Technologies, Inc., Santa Clara, CA (US)

( * ) Notice: Subject to any disclaimer, the term of this patent is extended or adjusted under 35 U.S.C. 154(b) by 156 days.

(21) Appl. No.: 15/138,568

(22) Filed: Apr. 26, 2016

(65) Prior Publication Data

US 2017/0310890 A1    Oct. 26, 2017

(51) Int. Cl.
*H04N 7/00* (2011.01)
*H04N 5/232* (2006.01)
(Continued)

(52) U.S. Cl.
CPC ....... *H04N 5/23238* (2013.01); *A61B 1/0011* (2013.01); *A61B 1/00096* (2013.01); *A61B 1/00186* (2013.01); *A61B 1/051* (2013.01); *B29C 43/021* (2013.01); *B29C 43/18* (2013.01); *B29D 11/00009* (2013.01); *B29D 11/00307* (2013.01); *G02B 9/10* (2013.01); *G02B 13/006* (2013.01); *G02B 13/0085* (2013.01); *H04N 5/2253* (2013.01); *H04N 5/2254* (2013.01); *B29D 11/0073* (2013.01);
*B29K 2063/00* (2013.01); *B29K 2105/20* (2013.01); *B29K 2701/00* (2013.01); *B29K 2709/08* (2013.01);
(Continued)

(58) Field of Classification Search
USPC .......................................... 348/36
See application file for complete search history.

(56) References Cited

U.S. PATENT DOCUMENTS

2011/0249169 A1   10/2011   Hsu et al.
2011/0255856 A1   10/2011   Reshidko et al.
(Continued)

OTHER PUBLICATIONS

Notice of Allowance corresponding to U.S. Appl. No. 15/138,510, dated Aug. 10, 2017.
(Continued)

*Primary Examiner* — Chikaodili E Anyikire
(74) *Attorney, Agent, or Firm* — Lathrop Gage LLP

(57) ABSTRACT

An ultra-small camera module with wide field of view includes (a) a wafer-level lens system for forming, on an image plane, an image of a wide field-of-view scene, wherein the wafer-level lens system includes (i) a distal planar surface positioned closest to the scene and no more than 2.5 millimeters away from the image plane in direction along optical axis of the wafer-level lens system, and (ii) a plurality of lens elements optically coupled in series along the optical axis, each of the lens elements having a curved surface, and (b) an image sensor mechanically coupled to the wafer-level lens system and including a rectangular array of photosensitive pixels, positioned at the image plane, for capturing the image, wherein cross section of the ultra-small camera module, orthogonal to the optical axis, is rectangular with side lengths no greater than 1.5 millimeters.

16 Claims, 17 Drawing Sheets

(51) Int. Cl.
| | |
|---|---|
| *H04N 5/225* | (2006.01) |
| *G02B 13/00* | (2006.01) |
| *G02B 9/10* | (2006.01) |
| *B29C 43/18* | (2006.01) |
| *B29C 43/02* | (2006.01) |
| *B29D 11/00* | (2006.01) |
| *A61B 1/05* | (2006.01) |
| *A61B 1/00* | (2006.01) |
| *G02B 5/20* | (2006.01) |
| *B29K 63/00* | (2006.01) |
| *B29K 105/20* | (2006.01) |
| *B29K 701/00* | (2006.01) |
| *B29K 709/08* | (2006.01) |
| *B29L 31/00* | (2006.01) |

(52) U.S. Cl.
CPC ......... *B29L 2031/753* (2013.01); *G02B 5/20* (2013.01); *H04N 2005/2255* (2013.01)

(56) References Cited

U.S. PATENT DOCUMENTS

2014/0128673 A1* 5/2014 Cheng ................ G02B 13/06
   600/109
2014/0334016 A1 11/2014 Yin et al.

OTHER PUBLICATIONS

U.S. Appl. No. 15/138,510, Office Action dated Apr. 4, 2017, 12 pages.

\* cited by examiner

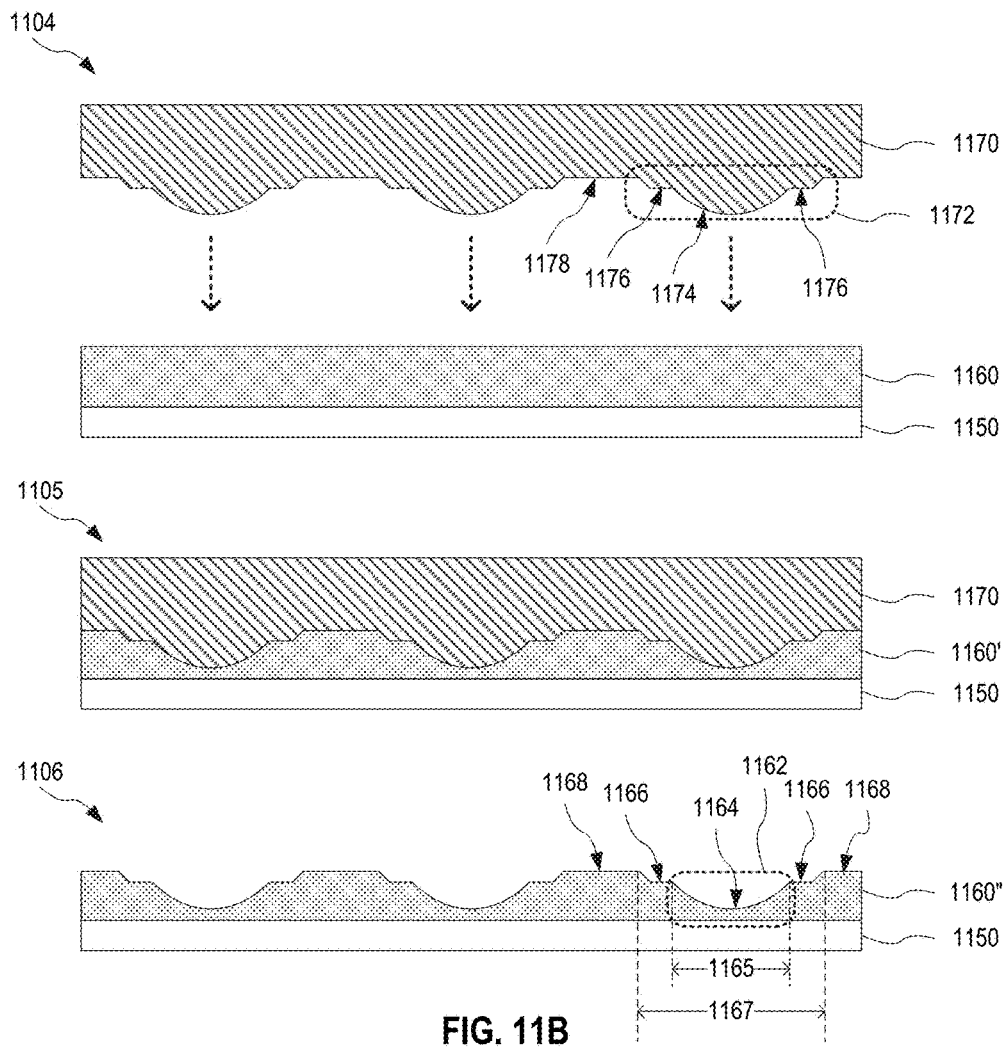
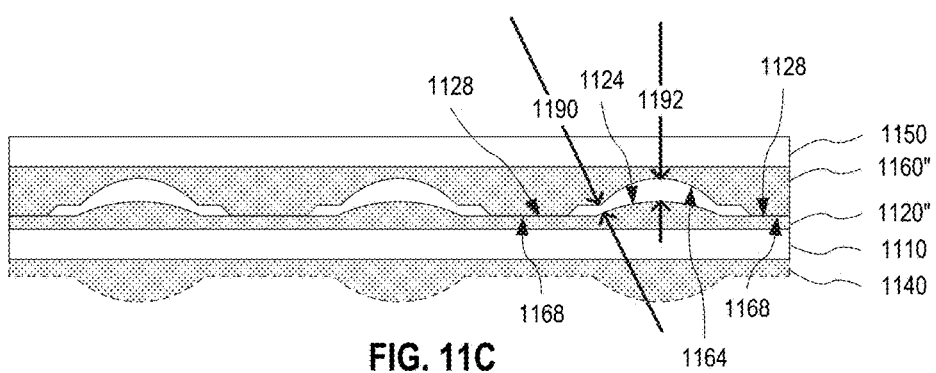
FIG. 11B
FIG. 11C

ULTRA-SMALL CAMERA MODULE WITH WIDE FIELD OF VIEW, AND ASSOCIATE LENS SYSTEMS AND METHODS

BACKGROUND

The demand for compact camera systems delivering high performance is increasing with the growing use of imaging systems in a wide variety of applications. Such applications are found in areas such as consumer electronics, machine vision, automotive, and medical diagnostics and procedures.

Medical endoscopes used to examine an interior part of the human body constitute an example with particularly challenging requirements to the size of the camera system. The camera system, including at least an image sensor, a lens system, and electronics, must fit within the area to be examined. Additionally, the camera system is often guided to the area of interest via passageways, such as an artery, which in itself imposes size constraints. Concurrently, high optical performance of the lens system of a medical endoscope camera system is desirable for achieving the goal of the procedure, for example an accurate diagnosis or a successful operation. However, the spatial requirements imposed by the use scenario limits the achievable performance of medical endoscope camera systems. Likewise, the size of conventional endoscope cameras limits the use of medical endoscopes.

SUMMARY

Disclosed herein are ultra-small camera modules with a wide field of view (FOV). These camera modules are suitable for employment in applications that are associated with tight spatial constraints and require good optical performance over a wide FOV, for example medical endoscopes. Also disclosed herein are lens systems for incorporation into the ultra-small camera modules as well as wafer-level methods for manufacturing the lens systems and ultra-small camera modules.

In an embodiment, an ultra-small camera module with a wide FOV includes a wafer-level lens system for forming, on an image plane, an image of a wide-FOV scene. The wafer-level lens system includes a distal planar surface positioned closest to the scene and no more than 2.5 millimeters away from the image plane in direction along optical axis of the wafer-level lens system. The wafer-level lens system further includes a plurality of lens elements optically coupled in series along the optical axis, each of the lens elements having a curved surface. In addition, the ultra-small camera module includes an image sensor. The image sensor is mechanically coupled to the wafer-level lens system and includes a rectangular array of photosensitive pixels, positioned at the image plane, for capturing the image. The cross section of the ultra-small camera module, orthogonal to the optical axis, is rectangular with side lengths no greater than 1.5 millimeters.

In an embodiment, a wafer-level method for manufacturing an ultra-small camera module with wide FOV includes molding a first lens layer onto a first substrate. The first lens layer is composed of a first planar layer and a plurality of convex lens surfaces protruding from the first planar layer in direction away from the first substrate. The method further includes molding a second lens layer onto a second substrate. The second lens layer is composed of a second planar layer and a plurality of recesses, the plurality of recesses forming a respective plurality of concave lens surfaces recessed from the second planar layer. Additionally, the method includes bonding the first planar layer directly to the second planar layer to form a composite wafer, such that the optical axes of the convex lens surfaces are aligned with the optical axes of the concave lens surfaces, respectively, with a gap between each of the convex lens surfaces and a corresponding one of the concave lens surfaces.

In an embodiment, an ultra-small wafer-level lens system for imaging a wide field of view includes a first substrate, a first lens element disposed on the first substrate, and a second substrate. The first lens element includes a concave lens surface facing away from the first substrate, and a first planar surface surrounding the concave lens surface and facing away from the first substrate. The lens system further includes a second lens element disposed on the second substrate. The second lens element includes a convex lens surface facing away from the second substrate, and a second planar surface surrounding the convex lens surface and facing away from the second substrate. The second planar surface is bonded to the first planar surface.

BRIEF DESCRIPTION OF THE DRAWINGS

FIGS. 11A-C illustrate one example of the method of FIG. 10.

DETAILED DESCRIPTION OF THE EMBODIMENTS

Figure 1:
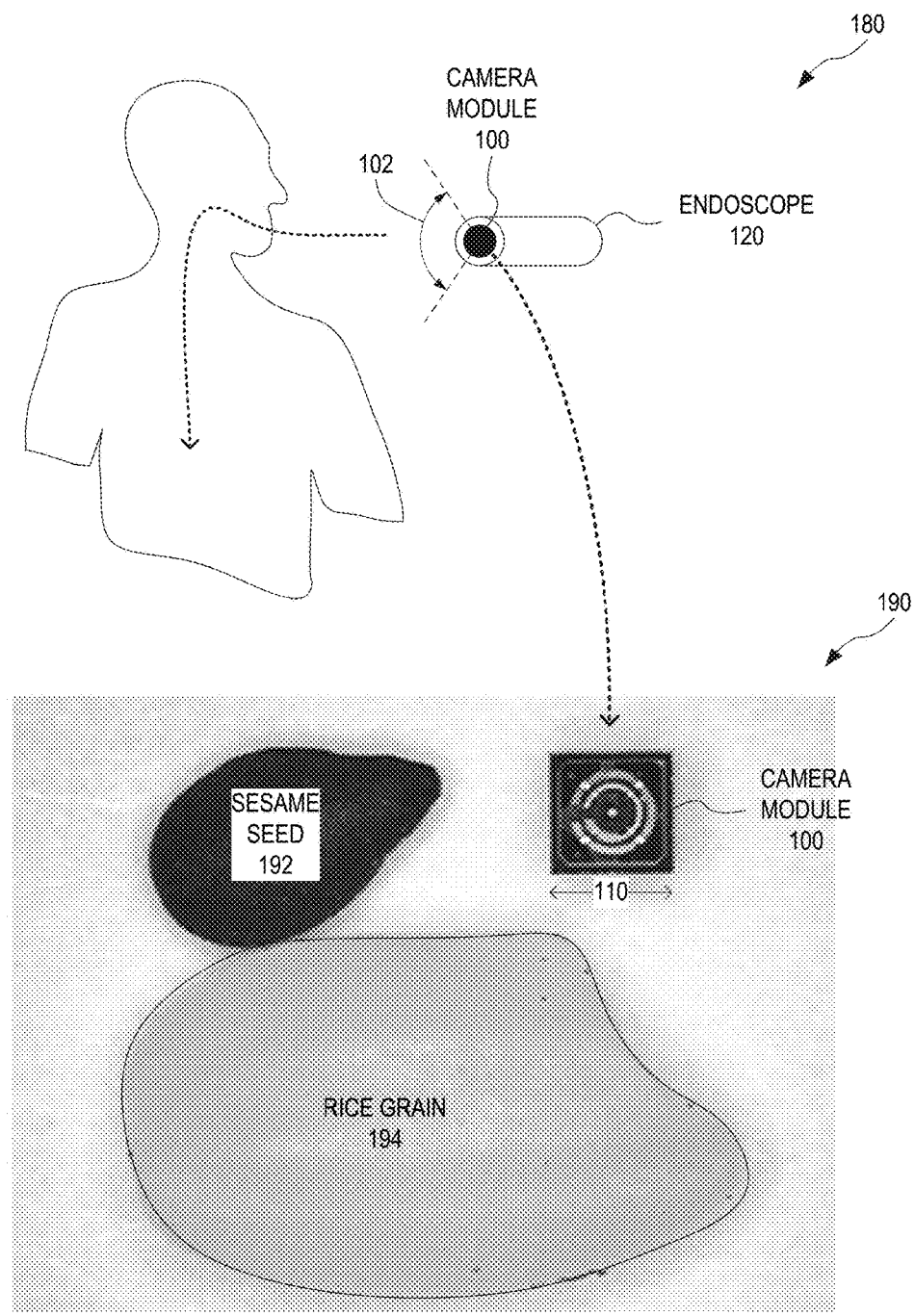
FIG. 1 illustrates an ultra-small camera module with a wide field of view, according to an embodiment.

FIG. 1 illustrates one exemplary ultra-small camera module 100 with a wide field of view (FOV) 102. Ultra-small camera module 100 is configured to produce an image of a wide-FOV scene. FIG. 1 shows a photograph 190 of one embodiment of ultra-small camera module 100, as well as an exemplary scenario 180 of use of ultra-small camera module 100. Photograph 190 depicts one embodiment of ultra-small camera module 100 next to a black sesame seed 192 and a rice grain 194, for size comparison. The viewing direction of photograph 190 is along the optical axis of ultra-small camera module 100.

Ultra-small camera module 100 has characteristic dimension 110 orthogonal to its optical axis. Characteristic dimension 110 is for example less than 1.5 millimeters (mm), such as in the range between 0.8 mm and 1.5 mm. In certain embodiments, FOV 102 is at least 90 degrees, for example in the range from 100 to 130 degrees, or at least 110 degrees.

By virtue of its ultra-small size, as indicated by characteristic dimension 110, and its wide FOV 102, ultra-small camera module 100 is ideally suited for implementation in a medical endoscope 120. Medical endoscope 120 may be a capsule endoscope ("pill camera"), or a more conventional wired endoscope configured to be inserted into the body of a patient while maintaining electrical connections to an exterior system. In either case, ultra-small camera module 100 offers significant advantages and facilitates the manufacture of smaller endoscopes than currently available. Ultra-small camera module 100 may offer similar advantages in other applications, such as consumer electronics products.

Figure 2A:
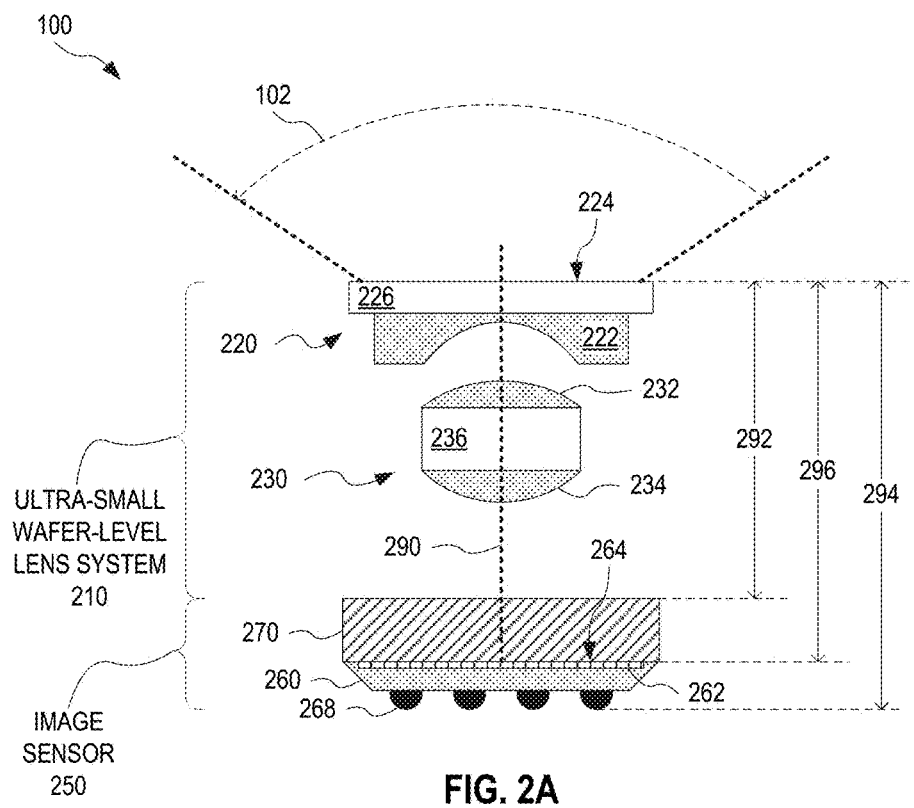
FIGS. 2A and 2B illustrate the ultra-small camera module of FIG. 1 in further detail, according to an embodiment.
Figure 2B:
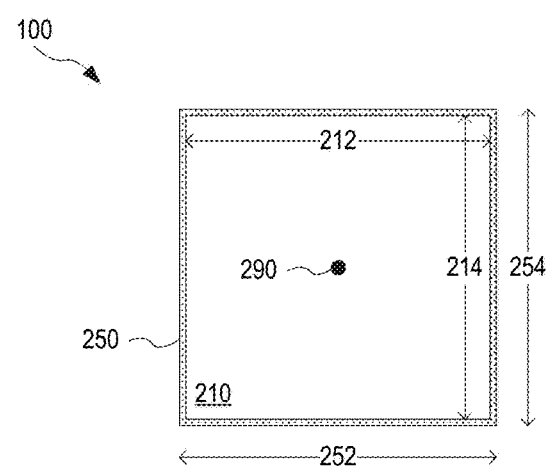

FIGS. 2A and 2B illustrate ultra-small camera module 100 in further detail. FIG. 2A is a cross-sectional view of ultra-small camera module 100, with the cross section being parallel with and including the optical axis 290 of ultra-small camera module 100. FIG. 2B is a top elevation view of ultra-small camera module 100 taken along optical axis 290. FIGS. 2A and 2B are best viewed together.

Ultra-small camera module 100 includes an ultra-small wafer-level lens system 210 and an image sensor 250. Lens system 210 includes a plurality of lens elements coupled in series along the optical axis, each of the lens elements having a curved surface. Herein, a "lens element" refers to an element that is at least partly transmissive to light and has a curved surface. Lens system 210 includes a substantially planar surface 224, which is the feature of lens system 210 closest to the scene to be imaged by ultra-small camera module 100 and furthest from image sensor 250. The embodiment of lens system 210, shown in FIG. 2A, includes a one-sided wafer-level lens 220 and a two-sided wafer-level lens 230. One-sided wafer-level lens 220 includes a substrate 226 and a concave lens element 222 disposed on the side of substrate 226 facing image sensor 250. Substrate 226 implements planar surface 224 as the surface of substrate 226 facing away from image sensor 250. Two-sided wafer-level lens 230 includes a substrate 236 and two concave lens elements 232 and 234. Lens element 232 is disposed on the side of substrate 236 facing away from image sensor 250. Lens element 234 is disposed on the side of substrate 236 facing image sensor 250.

Without departing from the scope hereof, lens system 210 may contain a different number of lens elements, and/or other additional optical components, between planar surface 224 and image sensor 250, as compared to the embodiment shown in FIG. 2A. For example, lens element 234 may be omitted, or lens system 210 may include an additional wafer-level lens between wafer-level lens 230 and image sensor 250. Likewise, the shapes of lens elements 222, 232, and 234 may be different from those shown in FIG. 2A, and the sizes of substrates 226 and 236 may be different from those shown in FIG. 2A, without departing from the scope hereof. For clarity of illustration, structures that mechanically couple together one-sided wafer-level lens 220, two-sided wafer-level lens 230, and image sensor 250 are not shown in FIGS. 2A and 2B.

Image sensor 250 includes an active layer 260 with photosensitive pixel array 262 located at, or near, a light-receiving surface 264 of active layer 260. Image sensor 250 further includes a cover glass 270 and a plurality of electrical contacts 268. For clarity of illustration, not all electrical contacts 268 are labeled in FIG. 2A. The number and/or arrangement of electrical contacts 268 may be different from what is shown in FIG. 2A, without departing from the scope hereof. Image sensor 250 is for example a complementary metal-oxide semiconductor (CMOS) image sensor or a charge coupled device (CCD) image sensor. Image sensor 250 and lens system 210 are positioned in relation to each other such that photosensitive pixel array 262 is substantially at the image plane of lens system 210.

In an embodiment, the total track length 296, along optical axis 290, of lens system 210 from planar surface 224 to the image plane of lens system 210 is no more than 2.5 mm, for example in the range from 1.5 to 2.5 mm. The length 292, along optical axis 290, of lens system 210 from planar surface 224 to image sensor 250 is in the range from 1.0 to 2.0 mm, for example. The total length 294 of ultra-small camera module 100, along optical axis 290, is in the range from 2.0 to 3.5 mm, for example.

One-sided wafer-level lens 220 and two-sided wafer-level lens 230 are produced at the wafer-level and therefore have rectangular cross section, when the cross section is orthogonal to optical axis 290. In one embodiment, all mechanical structures of lens system 210 are produced at the wafer level, and lens systems 210 are not singulated out of the wafer until after bonding together the individual optical elements of each lens system 210. In this embodiment, all of lens system 210 has the same rectangular cross sectional dimensions, when the cross section is orthogonal to optical axis 290. Image sensor 250 is also produced at the wafer-level and has rectangular cross section orthogonal to optical axis 290. FIG. 2B shows exemplary cross sectional dimensions of lens system 210 and image sensor 250. In this example, both of lens system 210 and image sensor 250 have rectangular cross section. Image sensor 250 has side lengths 252 and 254, and lens system 210 has side lengths 212 and 214. The cross section of lens system 210 may be smaller than the cross section of image sensor 250, as shown in FIG. 2B. Alternatively, the cross section of lens system 210 may be larger than the cross section of image sensor 250. In one embodiment, the cross section of both lens system 210 and image sensor 250 is substantially square, such that side lengths 212 and 214 are substantially the same and side lengths 252 and 254 are substantially the same. In an embodiment, each of side lengths 212, 214, 252, and 254 is no greater than 1.5 mm, for example in the range from 0.7 to 1.3 mm.

Figure 3:
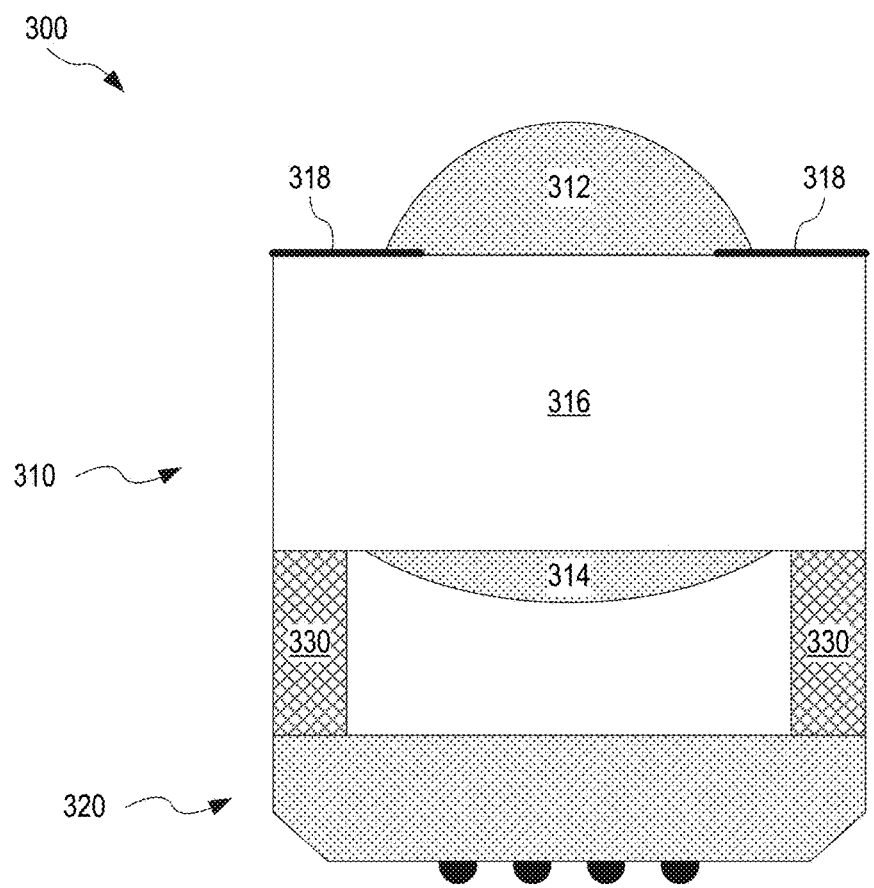
FIG. 3 shows a typical prior art wide-FOV camera module.

FIG. 3 shows a typical prior art wide-FOV camera module 300. Prior art wide-FOV camera module 300 includes a wafer-level lens 310, an image sensor 320, and a spacer 330 that couples wafer-level lens 310 to image sensor 320. Wafer-level lens 310 includes a substrate 316, two lens elements 312 and 314, and an aperture 318. Aperture 318 is an opaque coating deposited on a side of substrate 316 facing away from image sensor 320. This opaque coating has a centrally located opening that allows light from a scene to pass through wafer-level lens 310. Lens element 312 is disposed on the same side of substrate 316 as aperture 318, on top of a portion of aperture 318.

In order for wafer-level lens 310 to image a wide FOV, lens element 312 is a highly curved lens with a short radius of curvature. Lens element 312 thus has both a large extent away from substrate 316 and a large volume. The large extent of lens element 312 away from substrate 316 limits the ability to shrink the size of prior art wide-FOV camera module 300. In addition, the large volume of lens element 312 would be capable of deforming a thin version of substrate 316, and substrate 316 therefore must be made thick. This required thickness of substrate 316 further limits the ability to shrink the size of prior art wide-FOV camera module 300, both longitudinally (as explained in the foregoing) and laterally (that is, in dimension orthogonal to the optical axis). Laterally, the components of prior art wide-FOV camera module 300 must be made large to compensate for the large distance from lens element 312 to image sensor 320. Furthermore, it is challenging to produce lens element 312, due to its short radius of curvature, and the imaging performance of prior art wide-FOV camera module 300 is therefore compromised.

Referring again to FIGS. 2A and 2B, this embodiment of ultra-small wafer-level lens system 210 benefits from one-sided wafer-level lens 220 and its concave lens element 222 to eliminate the need for a highly curved lens element such as lens element 312. Thus, ultra-small wafer-level lens system 210 does not require a thick and highly curved convex lens element, such as lens element 312, and substrate 236 may be made significantly thinner than substrate 326. These factors help enable the short TTL 296, the short side lengths 212 and 214 of lens system 210, and the short side lengths 252 and 254 of image sensor 250.

Figure 4:
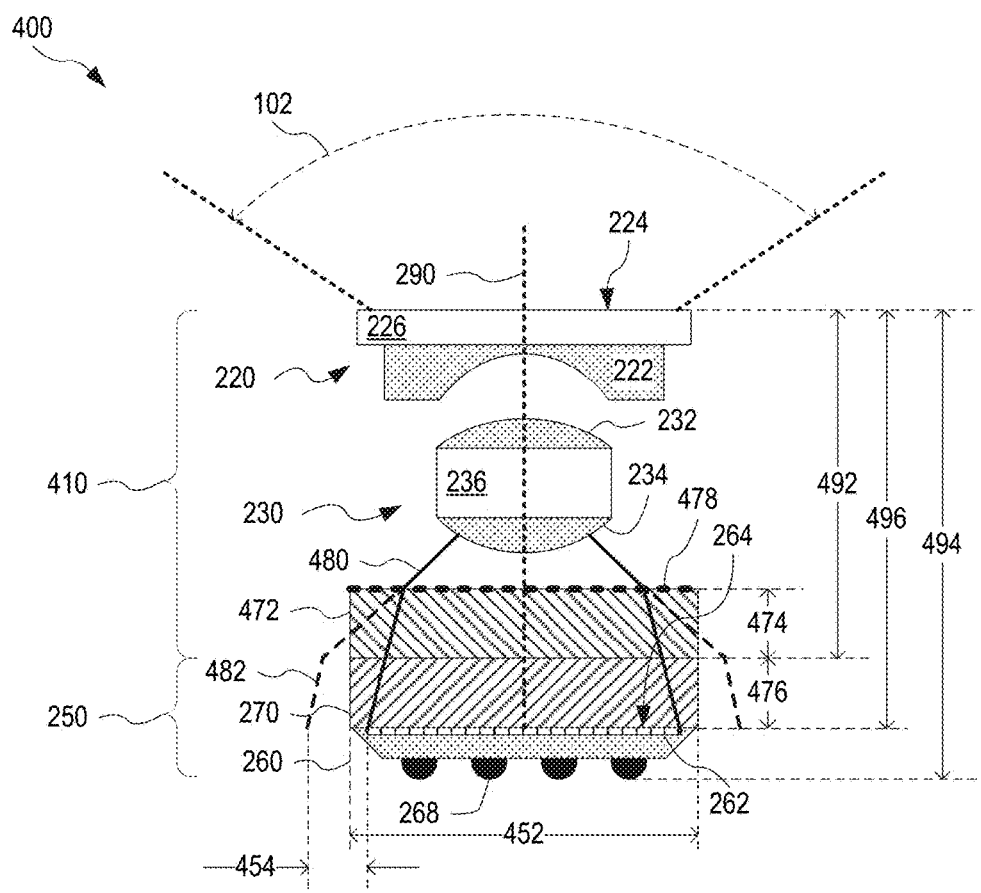
FIG. 4 illustrates an ultra-small, wide-FOV camera module that includes an additional transparent substrate to reduce the transverse extent of the image sensor, according to an embodiment.

FIG. 4 illustrates an ultra-small, wide-FOV camera module 400 that includes an additional transparent substrate 472 to reduce the transverse extent of the image sensor. Camera module 400 is an embodiment of ultra-small camera module 100 and has wide FOV 102. Camera module 400 includes an ultra-small wafer-level lens system 410 and image sensor 250. Lens system 410 is an embodiment of lens system 210. In addition to the components of lens system 210 shown in FIGS. 2A and 2B, lens system 410 includes a transparent substrate 472. When lens system 410 is implemented in camera module 400, transparent substrate 472 is in direct contact with cover glass 270. In one embodiment, lens system 410 is coupled with image sensor 250 by bonding transparent substrate 472 to cover glass 270.

Transparent substrate 472 is a substantially planar substrate made of, for example, glass or other optical material such as a polymer. Herein, "transparent" refers to being at least partly transmissive to light in the spectral range, within which photosensitive pixel array 262 is photosensitive.

Transparent substrate 472 is separated from wafer-level lens 230 by an air gap (or other medium of lower index of refraction than transparent substrate 472, such as a noble gas, if lens system 410 is implemented in such medium). Due to the higher index of refraction of transparent substrate 472 compared to the air gap, rays of light propagating at a non-zero angle relative to optical axis 290 toward image sensor 250 from wafer-level lens 230 are deflected by transparent substrate 472 to reduce the angle of such rays relative to optical axis 290. This is illustrated by exemplary rays 480 in FIG. 4. In the absence of transparent substrate 472, rays 480 would not be deflected until reaching cover glass 270, as illustrated by exemplary rays 482. The location of incidence of rays 482 onto the plane associated with array 262 is a distance 454 away from the location of incidence of rays 480 onto this plane. Accordingly, transparent substrate 472 enables use of an image sensor 250 with smaller transverse extent 452 than that required in the absence of transparent substrate 472. Transverse extent 452 represents a side length and is an example of side lengths 252 and 254. In certain implementations, transverse extent 452 is no greater than 1.5 mm.

In one embodiment, the thickness 474 of transparent substrate 472 is similar to the thickness 476 of cover glass 270. In another embodiment, thickness 474 is greater than thickness 476. Generally, thickness 476 may be in the range from 0.1 to 0.7 mm. The optimal value of thickness 474 is at least partly determined by a trade-off between the increased reduction in transverse extent resulting from an increased value of thickness 474, and a potential increase in the length 492 of lens system 410 resulting from a value of thickness 474 so large that the position of wafer-level lens 230 must be moved away from image sensor 250 to accommodate transparent substrate 472.

In an embodiment of lens system 410 configured to cooperate with an embodiment of image sensor 250 having thickness 476 of approximately 0.4 mm (or in the range from 0.3 to 0.5 mm), thickness 474 may be approximately 0.4 mm (or in the range from 0.3 to 0.5 mm). This value of thickness 474 may be advantageous for achieving a transverse extent 452 that is similar to the corresponding transverse extent of substrate 226. As thickness 474 is increased from zero, the achievable transverse extent 452 decreases. However, at a certain value of thickness 474, no additional benefit is obtainable because (a) the largest transverse extent of camera module 400 is the transverse extent of substrate 226 and/or (b) thickness 474 is so great that wafer-level lens 230 must be shifted away from image sensor 250 in order to accommodate transparent substrate 472. Thus, in an embodiment, thickness 474 is selected to approximately match transverse extent 452 to the corresponding transverse extent of substrate 226.

In an embodiment, the total track length 496, along optical axis 290, of lens system 410 from planar surface 224 to the image plane of lens system 410 is no more than 2.5 mm, for example in the range from 1.5 to 2.5 mm. The length 492, along optical axis 290, of lens system 410 from planar surface 224 to image sensor 250 is in the range from 1.0 to 2.0 mm, for example. The total length 494 of camera module 400, along optical axis 290, is in the range from 2.0 to 3.5 mm, for example.

In certain embodiments, lens system 410 further includes a wavelength filter 478 coated onto side of the transparent substrate 472 facing away from image sensor 250. Wavelength filter 478 is, for example, an infrared filter configured to block infrared light while allowing transmission of at least some visible light. In prior art camera module 300, such a filter is typically deposited on substrate 316 between lens element 312 and substrate 316. This positioning of the filter is known to lead to failures, either during or after manufacturing of prior art camera module 300, wherein lens element 312 peals away from substrate 316 due to the filter weakening the bond of lens element 312 with substrate 316. Lens system 410 overcomes this problem by positioning wavelength filter 478 on a surface that is not associated with a lens element.

Figure 5:
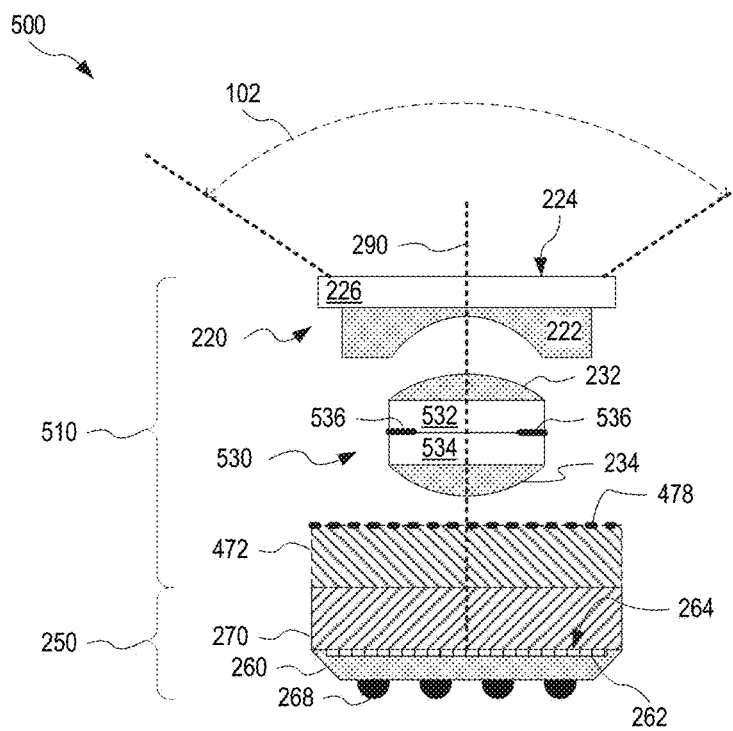
FIG. 5 illustrates one exemplary ultra-small, wide-FOV camera module that includes a stop aperture embedded in a composite substrate of a wafer-level lens, according to an embodiment.

FIG. 5 illustrates one exemplary ultra-small, wide-FOV camera module 500 that includes a stop aperture embedded in a composite substrate of a wafer-level lens. Camera module 500 is an embodiment of ultra-small camera module 100 and has wide FOV 102. Camera module 500 includes an ultra-small wafer-level lens system 510 and image sensor 250. Lens system 510 is an embodiment of lens system 210. As compared to the components of lens system 210 shown in FIGS. 2A and 2B, lens system 510 implements wafer-level lens 230 as a wafer-level lens 530. Optionally, lens system 510 also includes transparent substrate 472 as discussed above in reference to FIG. 4.

As compared to wafer-level lens 230, as shown in FIG. 2A, wafer-level lens 530 implements substrate 236 as a composite substrate that includes (a) a substrate 534 closer to image sensor 250 and supporting lens element 234, (b) a substrate 532 bonded to the side of substrate 534 facing away from image sensor 250, and (c) a stop aperture 536 disposed at the interface between substrates 532 and 534. Stop aperture 536 is an opaque material, such as an opaque coating, with an opening that allows transmission of light through wafer-level lens 530.

Herein, "opaque" refers to being at substantially opaque to light in the spectral range, within which photosensitive pixel array 262 is photosensitive.

By implementing a composite substrate, composed of substrates 532 and 534, lens system 510 enables placement of stop aperture 536 at a location, along optical axis 290, which is relatively centered between planar surface 224 and light-receiving surface 264. This positioning of stop aperture 536 helps reduce chromatic aberration.

Figure 6:
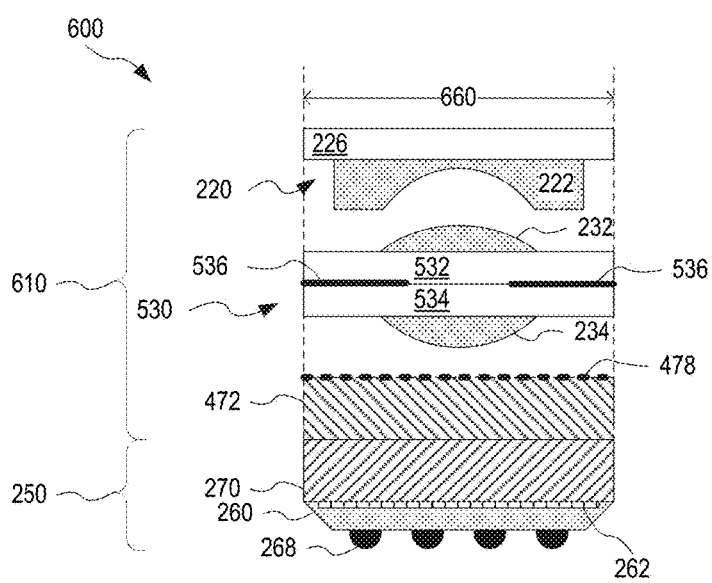
FIG. 6 illustrates an ultra-small, wide-FOV camera module with an ultra-small wafer-level lens system that includes a stop aperture embedded in a composite substrate of a wafer-level lens, according to an embodiment.

FIG. 6 illustrates one exemplary ultra-small, wide-FOV camera module 600 with an ultra-small wafer-level lens system 610 that includes a stop aperture embedded in a composite substrate of a wafer-level lens. Camera module 600 is an embodiment of ultra-small camera module 100 and has wide FOV 102. Camera module 600 includes ultra-small wafer-level lens system 610 and image sensor 250. Lens system 610 is an embodiment of lens system 510, which is diced from a wafer after coupling together wafer-level lens 220, wafer-level lens 530, and transparent substrate 472 (if included). As a result, in lens system 610, wafer-level lens 220, wafer-level lens 530, and transparent substrate 472 (if included) have same transverse extent 660. Transverse extent 660 represents a side length and is an example of side lengths 212 and 214. In certain implementations, transverse extent 660 is no greater than 1.5 mm.

In camera module 600, stop aperture 536 extends to the extreme transverse edges of substrates 532 and 534.

Figure 7:
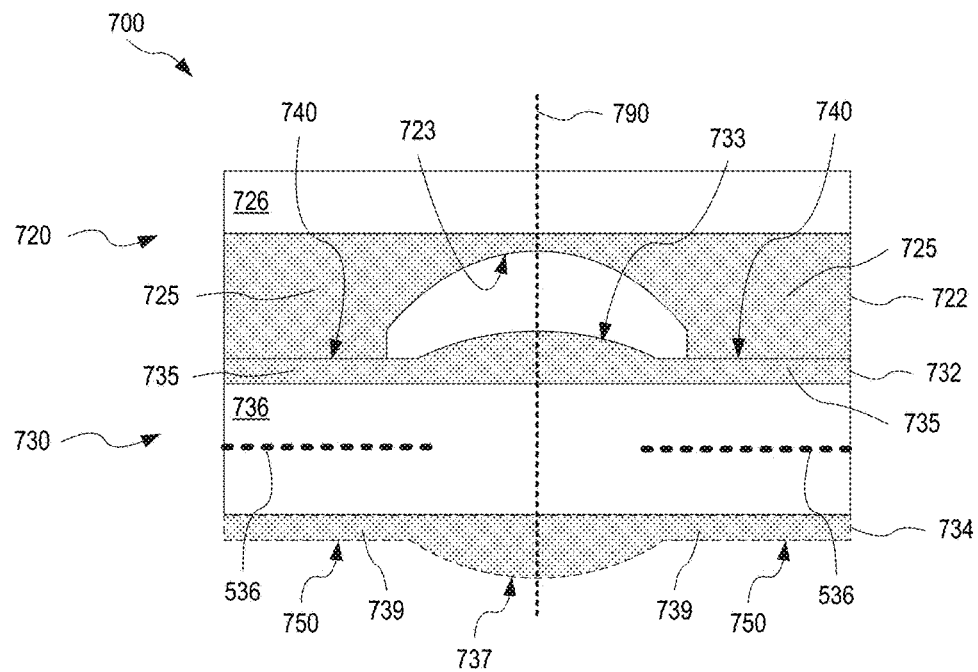
FIG. 7 illustrates one exemplary ultra-small, spacer-free lens system with a wide field of view, which is compatible with wafer-level manufacturing, according to an embodiment.

FIG. 7 illustrates one exemplary ultra-small, spacer-free lens system 700 with a wide FOV, which is compatible with wafer-level manufacturing. Lens system 700 is an embodiment of one-sided wafer-level lens 220 and at least a portion of two-sided wafer-level lens 230. Lens system 700 may be implemented in any one of lens systems 210, 410, 510, and 610. Lens system 700 includes two wafer-level lenses 720 and 730. Wafer-level lenses 720 and 730 are bonded directly to each other without a separate intervening spacer.

Wafer-level lens 720 includes a substrate 726 and a lens element 722 disposed thereon. Lens element 722 is integrally formed from a resin, such as an optical plastic. Substrate 726 is a glass or plastic substrate, for example. Wafer-level lens 720 is an embodiment of wafer-level lens 220. Lens element 722 includes (a) a concave lens surface 723 facing away from the substrate 726 and (b) a planar region 725 surrounding concave lens surface 723. Substrate 726 and lens element 722 are embodiments of substrate 226 and lens element 222, respectively.

Wafer-level lens 730 includes a substrate 736 and a lens element 732 disposed thereon. Lens element 732 includes (a) a convex lens surface 733 facing away from substrate 736 and (b) a planar region 735 surrounding convex lens surface 733. Lens element 722 is integrally formed from a resin, such as an optical plastic. Substrate 736 is a glass or plastic substrate, for example. Substrate 736 and lens element 732 are embodiments of substrate 236 and lens element 232, respectively.

Planar region 725 of lens element 722 is bonded directly to planar region 735 of lens element 732, at an interface 740, without a separate intervening spacer, thereby minimizing the distance between concave lens surface 723 and convex lens surface 733. The direct, spacer-free bonding of lens element 722 to lens element 732 helps facilitate making lens system 700 ultra small. The distance from concave lens surface 723 to convex lens surface 733 is fully determined by the geometry of lens elements 722 and 732. In one embodiment, the maximum distance between concave lens surface 723 and convex lens surface 733 is no more than 200 microns. Planar regions 725 and 735 may be bonded to each other using glue, for example a ultraviolet light curable glue or a thermosetting glue. Planar regions 725 and 735 are bonded to each other such that concave lens surface 723 and convex lens surface 733 share an optical axis 790. When planar regions 725 and 735 are bonded to each other, convex lens surface 733 protrudes into the recess in lens element 722 forming concave lens surface 723.

In certain embodiments, substrate 736 is a composite substrate that implements stop aperture 536, as discussed above for wafer-level lens 530 in reference to FIG. 5.

Optionally, wafer-level lens 730 further includes a lens element 734 disposed on the side of substrate 736 facing away from wafer-level lens 720. Lens element 734 may include (a) a convex lens surface 737 facing away from substrate 736 and (b) a planar region 739 surrounding convex lens surface 737, wherein planar region 739 forms a planar surface 750 facing away from substrate 736. Planar surface 750 is suitable for bonding to another planar structure, such as a spacer. Lens element 734 is integrally formed from a resin, such as an optical plastic. Lens element 734 may be composed of a material different from that of lens element 732. Embodiments of lens system 700 including lens element 734 are capable of imaging wide FOV 102.

An extension of lens system 700 further includes a lens element disposed on the side of substrate 726 facing away from wafer-level lens element 722.

Figure 8:
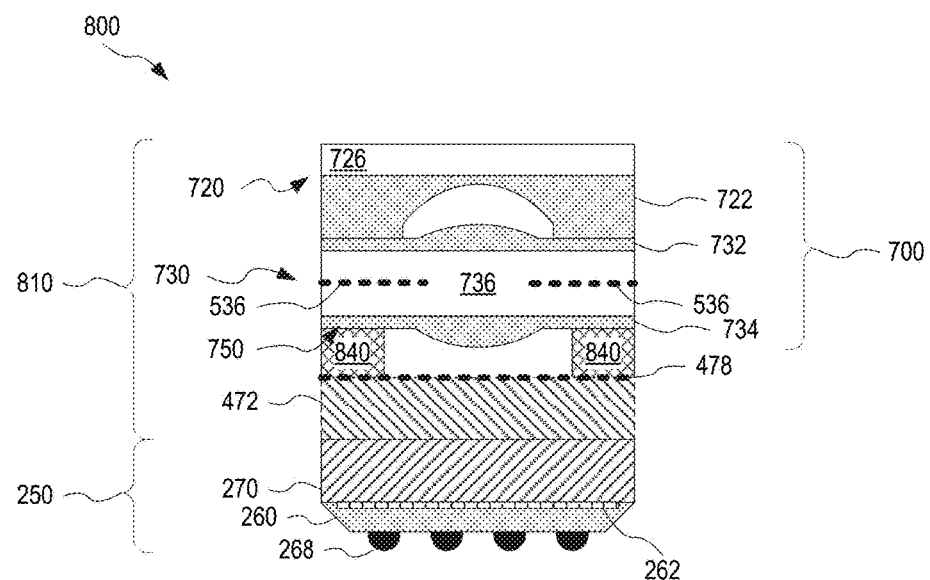
FIG. 8 illustrates one exemplary ultra-small, wide-FOV camera module including two wafer-level lenses bonded directly to each other in a spacer-free manner, according to an embodiment.

FIG. 8 illustrates one exemplary ultra-small, wide-FOV camera module 800 including two wafer-level lenses bonded directly to each other in a spacer-free manner. Camera module 800 is an embodiment of ultra-small camera module 100 and has wide FOV 102. Camera module 800 includes ultra-small, wafer-level lens system 810 and image sensor 250. Lens system 810 includes ultra-small, spacer-free lens system 700 with lens element 734, and a spacer 840. In one embodiment, spacer 840 is bonded to planar surface 750 of lens element 734. In another embodiment, lens system 810 further includes transparent substrate 472. In this embodiment, spacer 840 is bonded to planar surface 750 and transparent substrate 472, and transparent substrate 472 is bonded to cover glass 270. Optionally, lens system 810 includes wavelength filter 478 on transparent substrate 472.

Figure 9:
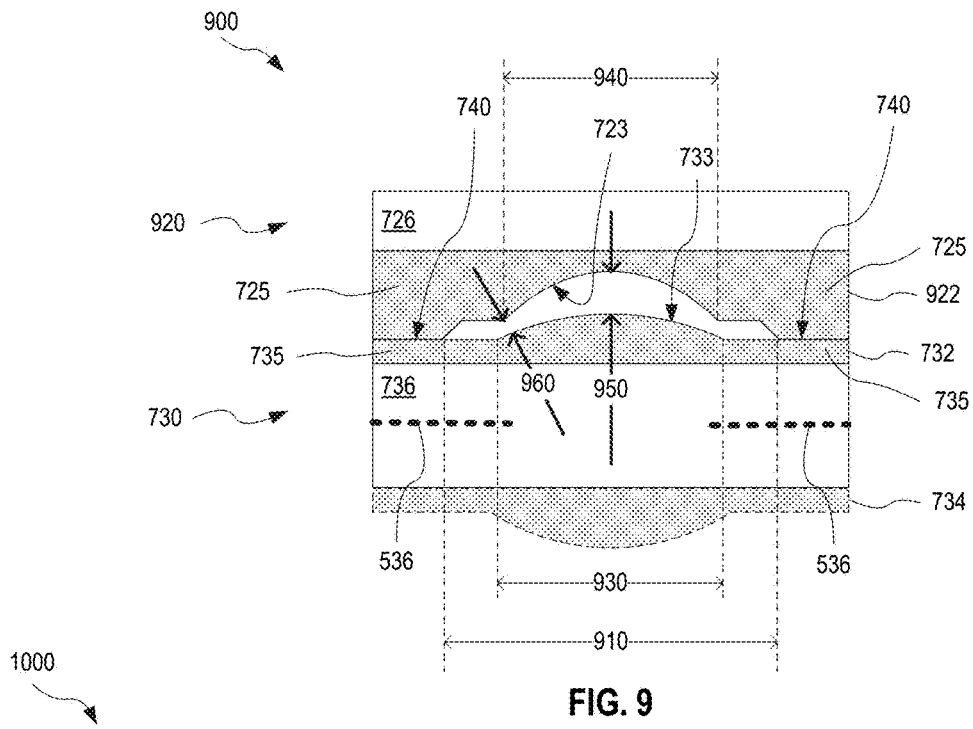
FIG. 9 illustrates another exemplary ultra-small, spacer-free lens system with a wide field of view, which is compatible with wafer-level manufacturing, according to an embodiment.

FIG. 9 illustrates another exemplary ultra-small, spacer-free lens system 900 with a wide field of view, which is compatible with wafer-level manufacturing. Lens system 900 is an embodiment of one-sided wafer-level lens 220 and at least a portion of two-sided wafer-level lens 230. Lens system 900 may be implemented in any one of lens systems 210, 410, 510, and 610. Lens system 900 is similar to lens system 700, except that wafer-level lens 720 is replaced by a wafer-level lens 920. Wafer-level lens 920 is similar to wafer-level lens 720, except that lens element 722 is replaced by a lens element 922. Lens element 922 includes (a) concave lens surface 723 facing away from the substrate 726 and (b) planar region 725 surrounding concave lens surface 723.

As compared to lens element 722, concave lens surface 723 is formed in a larger recess of lens element 922. This larger recess has diameter 910, while concave lens surface 723 has diameter 940. Diameter 910 is larger than diameter 940. Diameter 910 is also larger than the diameter 930 of convex lens surface 733. The larger recess diameter 910 accommodates convex lens surface 733, while leaving a minimum gap 960 between convex lens surface 733 and lens element 922. Larger recess diameter 910 may be particularly advantageous in embodiments of lens system 700, wherein diameter 930 is greater than diameter 940 (as shown in the example in FIG. 7) and/or concave lens surface 723 has smaller radius of curvature than convex lens surface 733. In such embodiments, larger recess diameter 910 allows for maintaining minimum gap 960 while achieving a desirably small maximum distance 950 between concave lens surface 723 and convex lens surface 733. Thus, larger recess diameter 910 further aids minimizing the size of lens system 900.

In one embodiment, minimum gap 960 is at least 50 microns, for example about 100 microns, while maximum distance 950 is no more than 200 microns. A minimum gap 960 of at least 50 microns improves the manufacturability of lens system 900, as compared to a smaller value of minimum gap 960.

Figure 10:
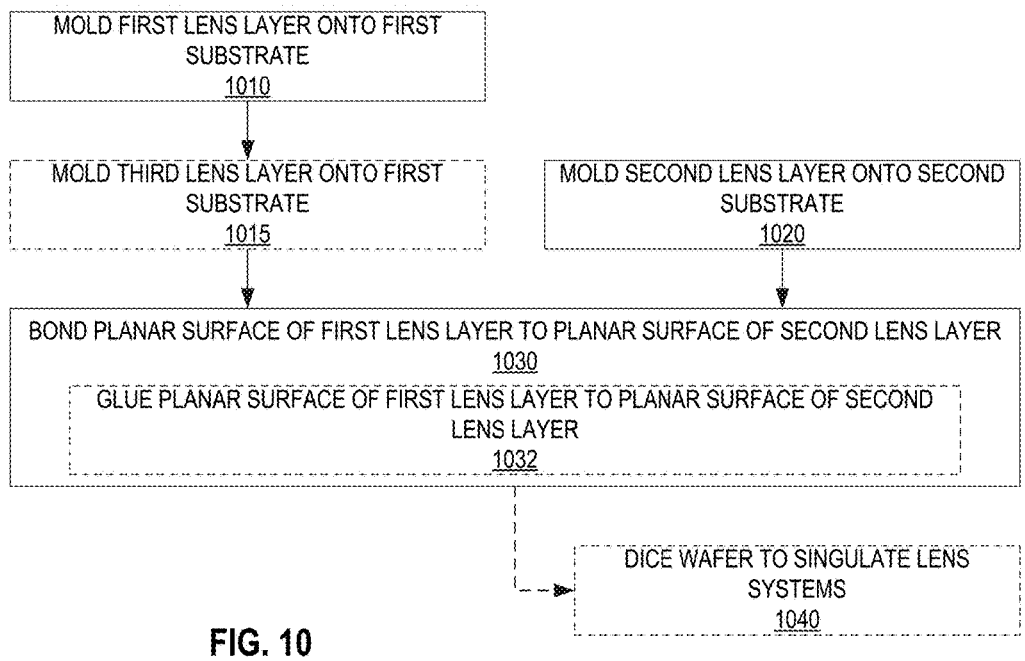
FIG. 10 illustrates a wafer-level method for manufacturing a plurality of spacer-free composite lens systems with wide FOV, according to an embodiment.

FIG. 10 illustrates one exemplary wafer-level method 1000 for manufacturing a plurality of spacer-free composite lens systems with wide FOV, such as lens system 700 or lens system 900.

In a step 1010, method 1000 molds a first lens layer onto a first substrate. This first lens layer includes a plurality of convex lens surfaces protruding from an otherwise substantially planar surface of the first lens layer.

In a step 1020, method 1000 molds a second lens layer onto a second substrate. This second lens layer includes a plurality of concave lens surfaces recessed from an otherwise substantially planar surface of the second lens layer.

A step 1030 bonds a planar surface of the first lens layer to a planar surface of the second lens layer, such that the optical axes of the convex lens surfaces are aligned with the optical axes of the concave lens surfaces, respectively, and such that the convex lens surfaces protrudes into recesses of the second lens layer. Each convex lens surface of the first lens layer is surrounded by a segment of the planar surface bonded to the second lens layer. Similarly, each concave lens surface of the second lens layer is surrounded by a segment of the planar surface bonded to the first lens layer.

In an embodiment, step 1030 implements a step 1032 of gluing the planar surface of the first lens layer to the planar surface of the second lens layer. Step 1032 may utilize ultraviolet curable glue or a thermosetting glue.

In an embodiment, method 1000 further includes a step 1040 of dicing the composite wafer formed in step 1030 to singulate a plurality of composite lens systems therefrom. Each composite lens system includes a convex lens surface and a concave lens surface facing each other.

Optionally, method 1000 further includes a step 1015 of molding a third lens layer onto the side of the first substrate facing away from the first lens layer. This third lens layer includes a plurality of lens surfaces respectively aligned with the convex lens surfaces of the first lens layer. Also indicated in FIG. 10 as being performed between steps 1010 and 1030, step 1015 may be performed between steps 1030 and 1040.

Figure 11A:
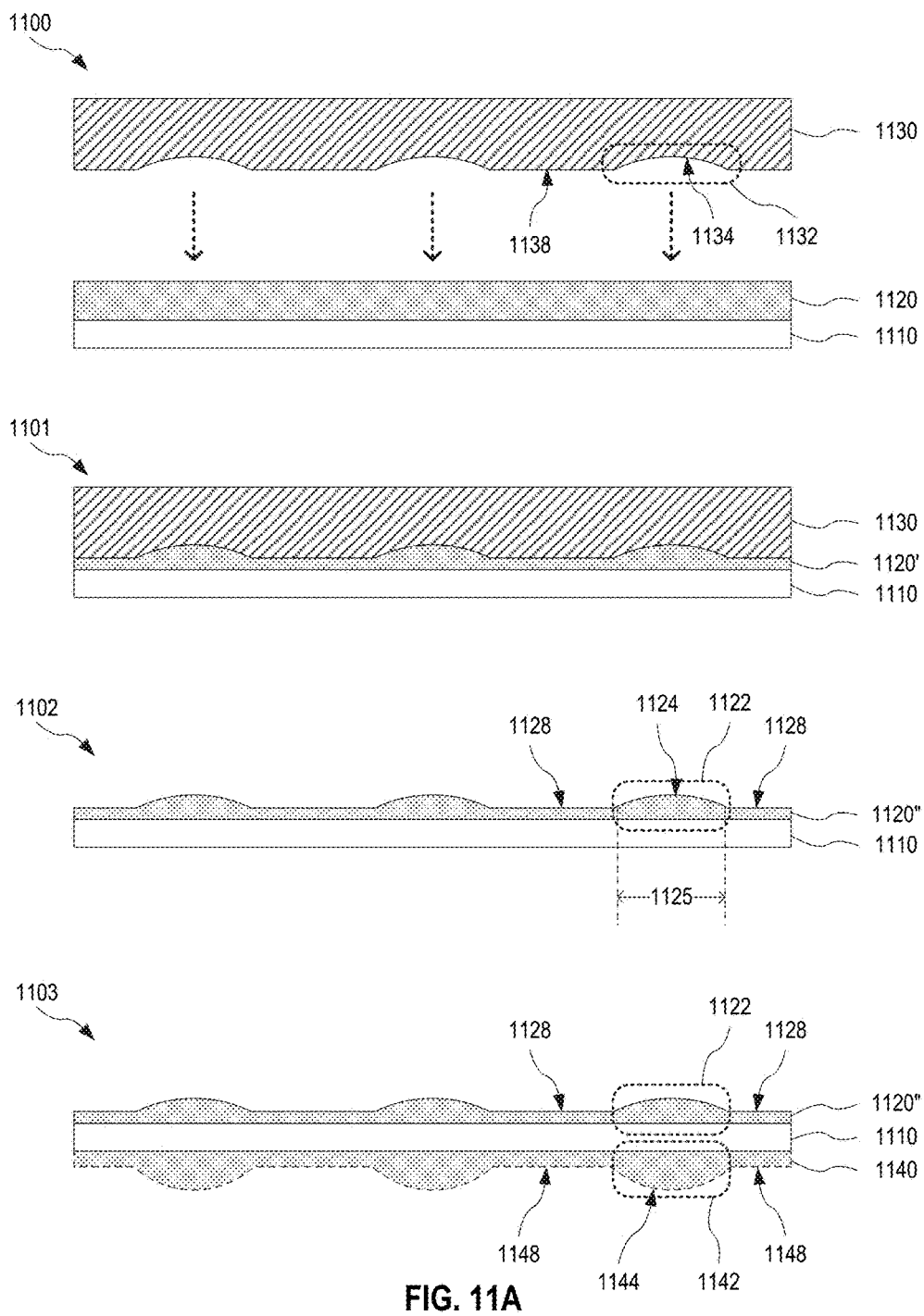

FIGS. 11A-C is a series of diagrams illustrating one example of method 1000. FIG. 11A illustrates one example of step 1010, optionally together with step 1015. FIG. 11B illustrates one example of step 1020. FIG. 11C illustrates one example of step 1030. FIGS. 11A-C are best viewed together.

Diagrams 1100 and 1101 illustrate the process of molding the first lens layer in step 1010, in this example. A resin 1120 is deposited on a substrate 1110, and a mold 1130 is pressed onto resin 1120 to form a shaped resin layer 1120'. Mold 1130 has a planar surface 1138 with recesses 1132 formed therein. Each recess 1132 includes a concave surface 1134. It will be appreciated that mold 1130 generally has many more recesses 1132 than shown in FIG. 11A. As shown in diagram 1102, this example of step 1010 produces a lens layer 1120" on substrate 1110. Lens layer 1120" includes a plurality of convex lens elements 1122, each including a convex lens surface 1124 and each surrounded by a planar surface 1128.

Optionally, as shown in diagram 1103, a lens layer 1140 is formed, in step 1015, on the side of substrate 1110 facing away from lens layer 1120". Lens layer 1140 includes a plurality of lens elements 1142, each having a curved lens surface 1144 and each surrounded by a planar surface 1148. Curved lens surface 1144 may be convex and protruding from planar surface 1148, as depicted in diagram 1103, or be concave and recessed from planar surface 1148 without departing from the scope hereof. Each lens element 1142 is aligned with a corresponding convex lens element 1122.

Diagrams 1104 and 1105 illustrate the process of molding the second lens layer in step 1020 of method 1000, in this example. A resin 1160 is deposited on a substrate 1150, and a mold 1170 is pressed onto resin 1160 to form a shaped resin layer 1160'. Mold 1170 has a planar surface 1178 with protrusions 1172 formed thereon. Each protrusion 1172 includes a convex surface 1174. It will be appreciated that mold 1170 generally has many more protrusions 1172 than shown in FIG. 11B. As shown in diagram 1105, this example of step 1020 produces a lens layer 1160" on substrate 1150. Lens layer 1160" includes a plurality of concave lens elements 1162, each including a concave lens surface 1164. Each concave lens surface 1164 is recessed from planar surface 1168.

In one embodiment, as illustrated in FIG. 11B, each protrusion 1172 is larger than convex surface 1174 and further includes a larger diameter pedestal 1176. The shape of pedestal 1176 may differ from that shown in FIG. 11B, without departing from the scope hereof. In this embodiment, each concave lens surface 1164 is nested inside a larger recess 1166. The diameter 1167 is greater than the diameter 1165 of concave lens surface 1164.

FIG. 11C shows bonding of lens layer 1120" to lens layer 1160" in step 1030. Planar surface 1128 is bonded to planar surface 1168, for example using a glue as discussed above in reference to step 1032 and FIG. 10. When lens layers 1120" and 1160" are bonded to each other as shown in FIG. 11C, each convex lens surface 1124 is aligned with a corresponding concave lens surface 1164, and each convex lens surface 1124 protrudes into a corresponding recess of lens layer 1160".

In an embodiment, the minimum gap 1190 between convex lens surface 1124 and lens layer 1160" is at least 50 microns, for example approximately 100 microns, and the maximum distance 1192 between convex lens surface 1124 and concave lens surface 1164 is no more than 200 microns.

For clarity of illustration, not all instances of replicate elements are labeled in FIGS. 11A-C.

Figure 12:
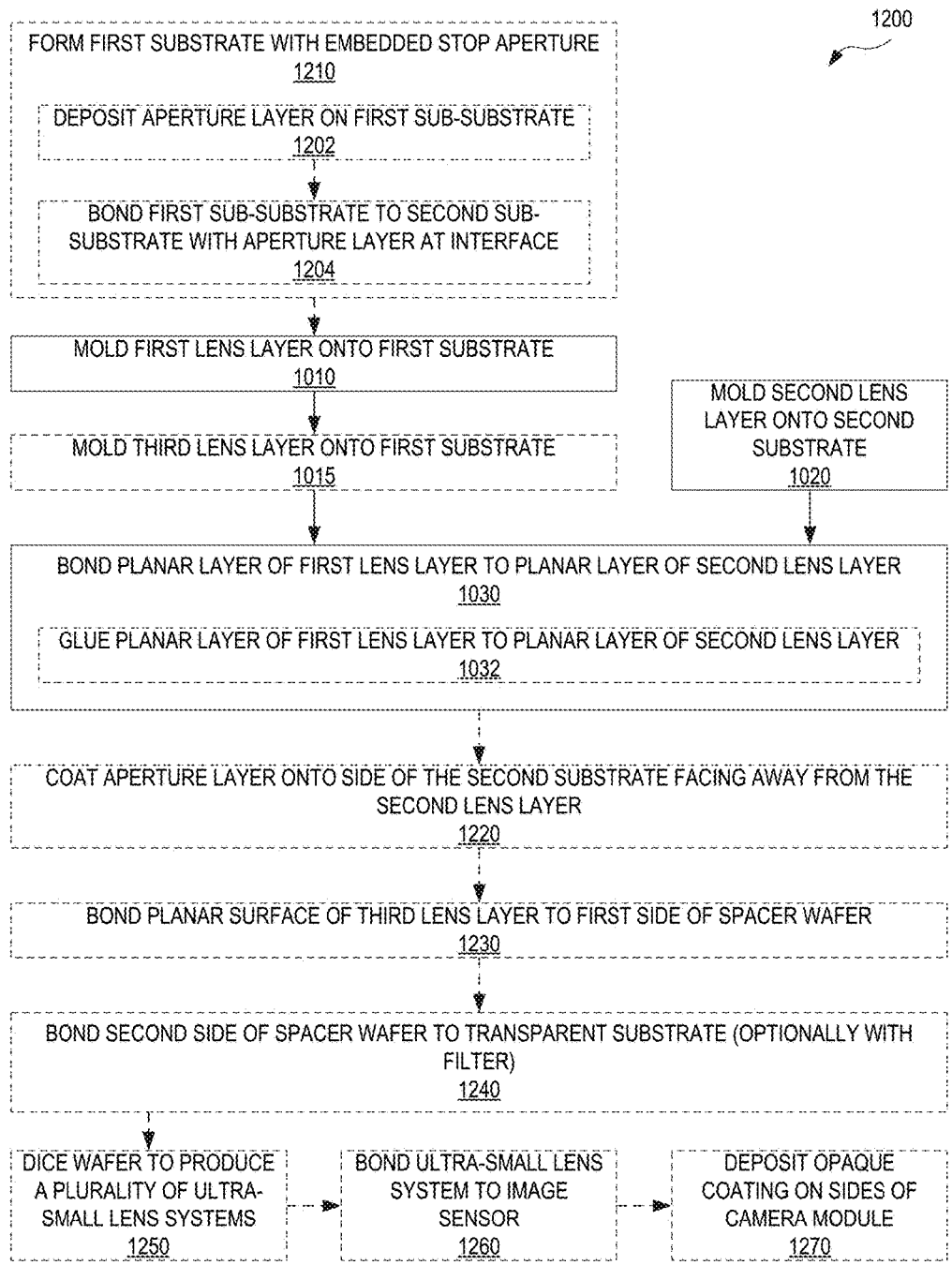
FIG. 12 illustrates one exemplary wafer-level method for manufacturing an ultra-small camera module, according to an embodiment.

FIG. 12 illustrates one exemplary wafer-level method 1200 for manufacturing an ultra-small camera module, such as ultra-small camera module 100 or one of its embodiments, ultra-small camera modules 400, 500, 600, and 800.

Method 1200 includes steps 1010, 1020, and 1030, and optionally step 1015, of method 1000, as discussed above in reference to FIG. 10. In one example, method 1200 performs steps 1010, 1020, and 1030, and optionally step 1015, of method 1000, as discussed above in reference to FIGS. 11A-C.

In an embodiment, method 1200 includes a step 1210 of forming the first substrate of step 1010 with an embedded stop aperture. Step 1210 includes two steps 1202 and 1204. Step 1202 deposits an aperture layer on a first sub-substrate. The aperture layer is an opaque layer with a plurality of openings. Step 1204 bonds the first sub-substrate to a second sub-substrate such that the aperture layer is placed at the interface between the first and second sub-substrates.

Figure 13:
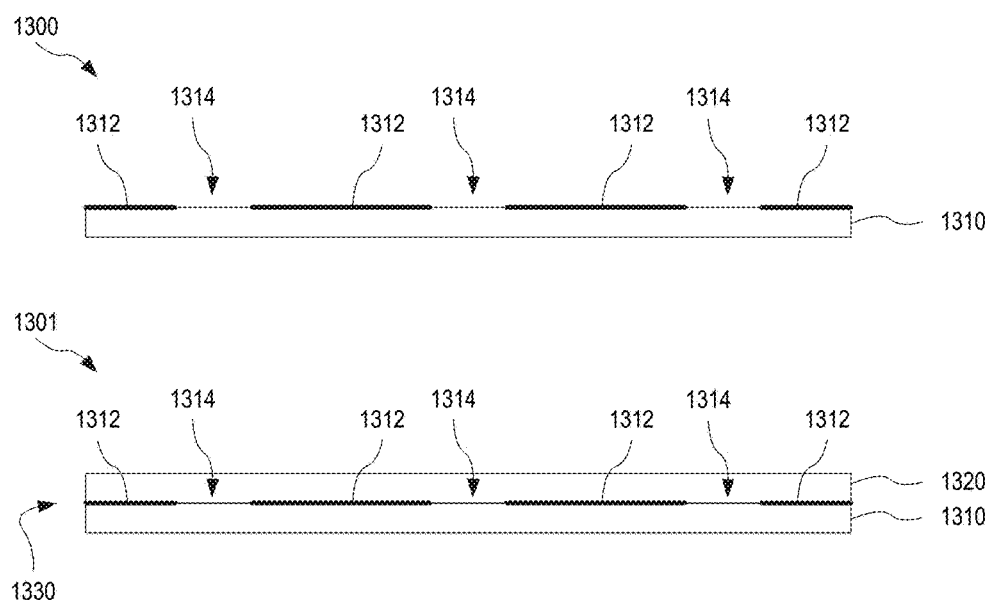
FIG. 13 illustrates one example of a step of forming a substrate with an embedded stop aperture in the method of FIG. 12.

FIG. 13 illustrates one example of step 1210. The example of FIG. 13 is related to that of FIGS. 11A-C. In diagram 1300, an aperture layer 1312 is deposited on a sub-substrate 1310. Aperture layer 1312 in an opaque layer with openings 1314 through which light may pass. In diagram 1301, a sub-substrate 1320 is bonded to the side of sub-substrate 1310 associated with aperture layer 1312. The resulting composite substrate may be implemented in the example of FIGS. 11A-C as substrate 1110.

Referring again to FIG. 12, an embodiment of method 1200 includes a step 1220 of coating an aperture layer onto the side of the second substrate (of step 1020) facing away from the first substrate.

Figure 14:
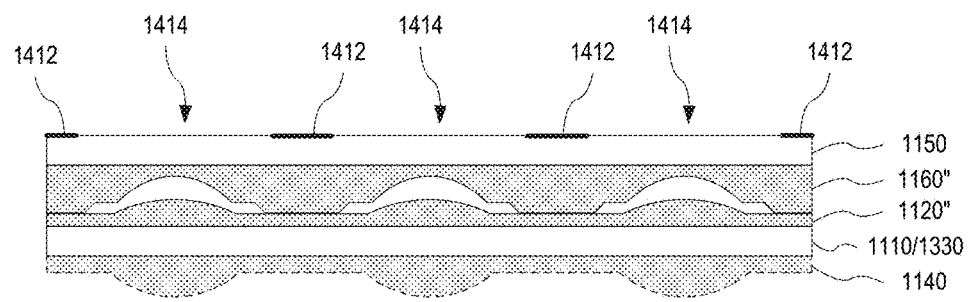
FIG. 14 illustrates one example of a step of forming an aperture in the method of FIG. 12.

FIG. 14 illustrates one example of step 1220. The example of FIG. 14 is related to that of FIGS. 11A-C and 13. In the example of FIG. 14, an aperture layer 1412 is deposited on substrate 1150. Aperture layer 1412 is an opaque layer with openings 1414 through which light may pass.

Referring again to FIG. 12, an embodiment of method 1200 includes a step 1230 of bonding a planar surface of the third lens layer to the first side of a spacer wafer.

Figure 15:
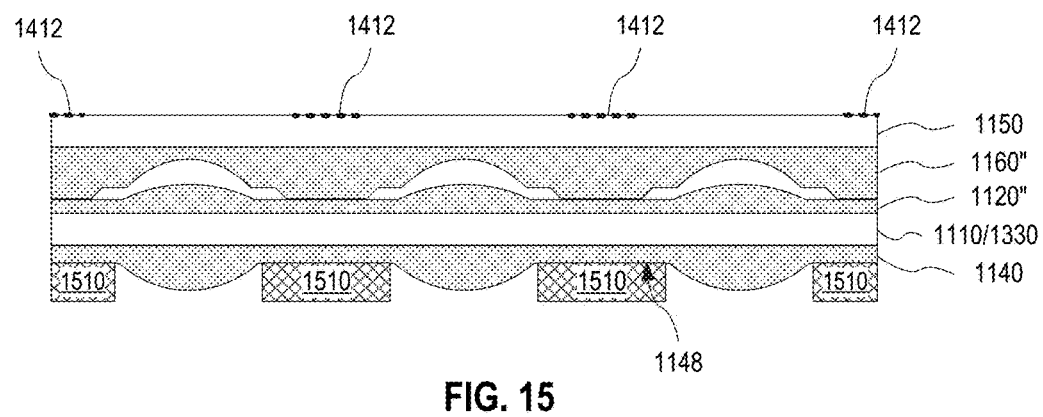
FIG. 15 illustrates one example of a step of incorporating a spacer wafer into a lens system in the method of FIG. 12.

FIG. 15 illustrates one example of step 1230. The example of FIG. 15 is related to that of FIGS. 11A-C, 13, and 14. In the example of FIG. 15, a spacer wafer 1510 is bonded to a planar surface 1148 of lens layer 1140.

Referring again to FIG. 12, an embodiment of method 1200 includes a step 1240 of bonding a second side of the spacer wafer, facing away from the third lens layer, to a transparent substrate. Optionally, the transparent substrate includes a wavelength filter.

Figure 16:
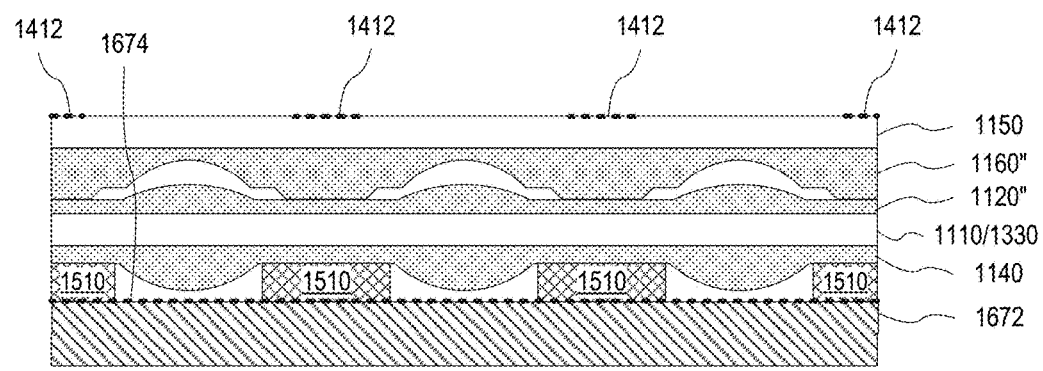
FIG. 16 illustrates one example of a step of incorporating a transparent substrate into a lens system in the method of FIG. 12.

FIG. 16 illustrates one example of step 1240. The example of FIG. 16 is related to that of FIGS. 11A-C, 13-15. In the example of FIG. 16, a transparent substrate 1672 is bonded to spacer wafer 1510. Optionally, transparent substrate 1672 has a wavelength filter 1674 deposited thereon. Wavelength filter 1674 is, for example, an infrared filter configured to block infrared light while allowing transmission of at least some visible light.

Referring again to FIG. 12, an embodiment of method 1200 includes a step 1250 of dicing the wafer to singulate therefrom a plurality of ultra-small lens systems, wherein the wafer is that resulting from completion of any one of steps 1030, 1220, 1230, and 1240.

Figure 17:
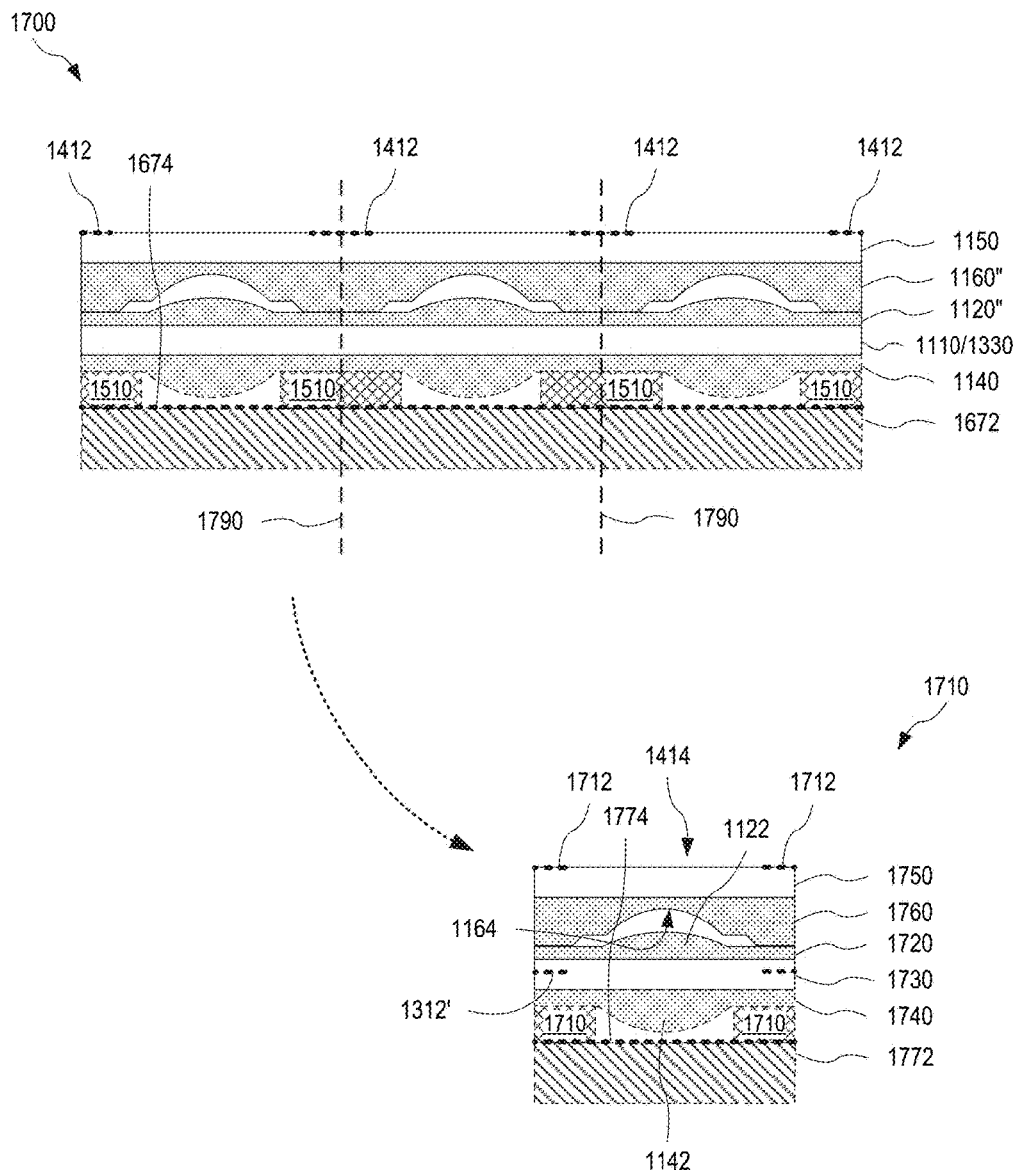
FIG. 17 illustrates one example of a step of dicing a wafer to produce a plurality of ultra-small lens systems in the method of FIG. 12.

FIG. 17 illustrates one example of step 1250. The example of FIG. 17 is related to that of FIGS. 11A-C, 13-16. In the example of FIG. 17, the composite wafer of FIG. 11, FIG. 14, FIG. 15, or FIG. 16 is diced along dicing lines 1790 to produce a plurality of ultra-small lens systems 1710. In one embodiment, ultra-small lens system 1710 is lens system 210. In another embodiment, ultra-small lens system 1710 is lens system 410. In yet another embodiment, ultra-small lens system 1710 is either one of lens system 510 and lens system 610. In a further embodiment, ultra-small lens system 1710 is either one of lens systems 700 and 810.

Referring again to FIG. 12, an embodiment of method 1200 includes a step 1260 of bonding each of at least some of the ultra-small lens systems of step 1250 to an image sensor.

Figure 18:
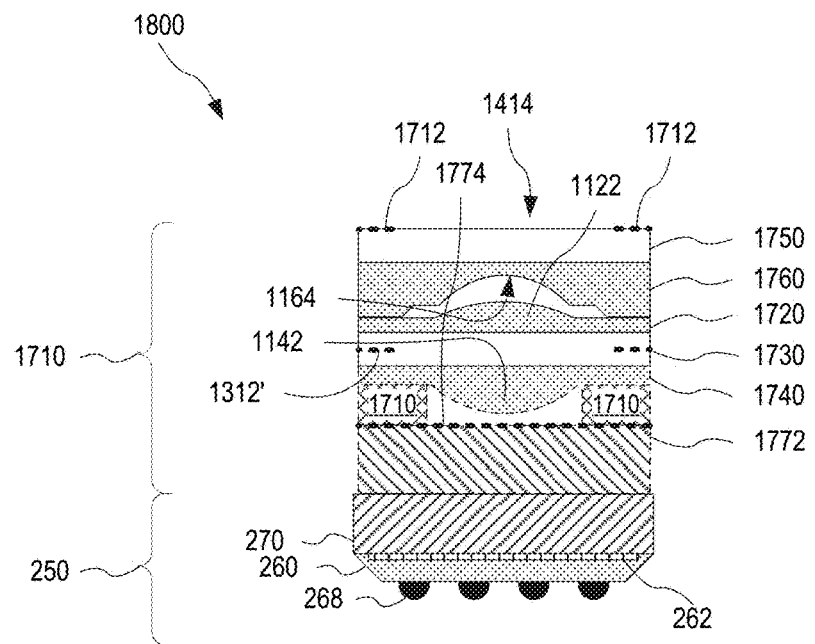
FIG. 18 illustrates one example of step of bonding ultra-small lens systems to image sensors in the method of FIG. 12.

FIG. 18 illustrates one example of step 1260. The example of FIG. 18 is related to that of FIGS. 11A-C, 13-17. In the example of FIG. 18, ultra-small lens system 1710 is bonded to image sensor 250 to form an ultra-small camera module 1800. In one embodiment, ultra-small camera module 1800 is camera module 200. In another embodiment, ultra-small camera module 1800 is camera module 400. In yet another embodiment, ultra-small camera module 1800 is either one of camera module 500 and camera module 600. In a further embodiment, ultra-small camera module 1800 is camera module 800. Although FIG. 18 shows image sensor 250 as having larger transverse extent (orthogonal to the optical axis) than lens system 1710, the transverse extent of image sensor 250 may be the same as or less than the transverse extent of lens system 1710.

Referring again to FIG. 12, an embodiment of method 1200 includes a step 1270 of depositing an opaque coating on the sides of the camera module, wherein the sides face away from the optical axis of the camera module. This opaque coating prevents light from entering the camera module and being detected by the image sensor without being properly imaged by the lens system.

Figure 19:
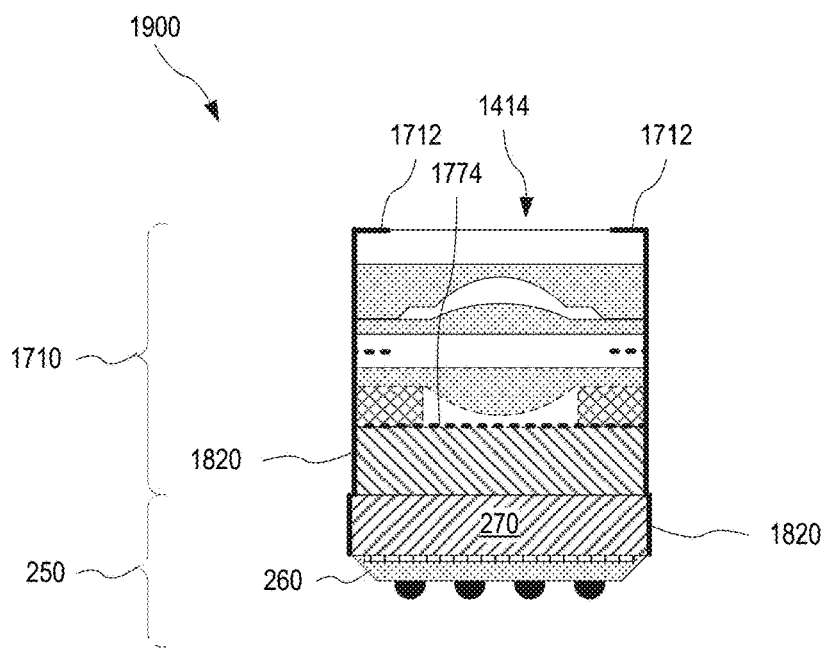
FIG. 19 illustrates one example of light shielding camera modules in the method of FIG. 12.

FIG. 19 illustrates one example of step 1270. The example of FIG. 19 is related to that of FIGS. 11A-C, 13-18. In the example of FIG. 19, an opaque coating 1820 is deposited on sides of lens system 1710 and image sensor 250, which are otherwise not opaque, so as to form a shielded ultra-small camera module 1900. Shielded ultra-small camera module 1900 is an embodiment of any one of ultra-small camera modules 100, 400, 500, 600, 800, and 1800.

Figure 20:
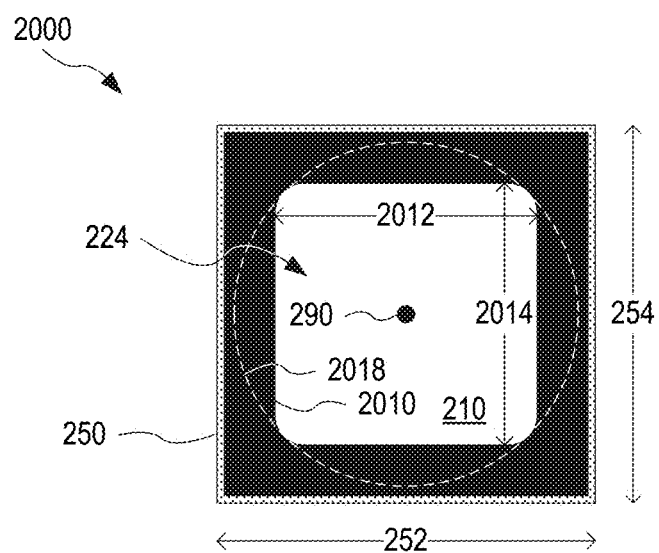
FIG. 20 illustrates an ultra-small camera module having a wide FOV and a rounded rectangular aperture for optimally efficient blockage of undesirable light entry into the ultra-small camera module, according to an embodiment.

FIG. 20 illustrates one exemplary ultra-small camera module 2000 having a wide FOV and a rounded rectangular aperture 2010 for optimally efficient blockage of undesirable light entry into ultra-small camera module 100. Rounded rectangular aperture 2010 may be applied to any one of ultra-small camera modules 100, 400, 500, 600, 800, 1800, and 1900. Thus, ultra-small camera module 2000 is an embodiment of any one of ultra-small camera modules 100, 400, 500, 600, 800, 1800, and 1900. FIG. 20 shows ultra-small camera module 2000 in the same view as used for FIG. 2B.

Rounded rectangular aperture 2010 is an opaque material, such as a coating, deposited on planar surface 224 of lens system 210. Rounded rectangular aperture 2010 has an opening that is shaped as a rounded rectangle and allows passage of light from a scene into lens system 210, so as to be imaged by lens system 210 onto image sensor 250 for detection by image sensor 250. Away from the rounded corners, the opening of rounded rectangular aperture 2010 has widths 2012 and 2014. Width 2012 is parallel to side length 252, and width 2014 is parallel to side length 254. In an embodiment, the opening of rounded rectangular aperture 2010 has substantially the same aspect ratio as photosensitive pixel array 262 of image sensor 250. In one implementation, the rounded portions of the opening of rounded rectangular aperture 2010 occupies about 5 to 30 percent of each of widths 2012 and 2014.

For comparison, a conventional circular aperture 2018 is overlaid on FIG. 20. It is clear that circular aperture 2018 is not optimized for the rectangular shape of photosensitive pixel array 262 of image sensor 250. Conventional circular aperture 2018 allows light to enter the camera module outside the desirable rectangular area and therefore does not effective block light along the sides of planar surface 224 away from its corners. Therefore, circular aperture 2018 may produce vignetting in images captured by photosensitive pixel array 262. Although it is possible to decrease the opening of circular aperture 2018 to improve light blockage along the sides of planar surface 224, this may lead to inefficient light transmission to the corners of photosensitive pixel array 262. In contrast, rounded rectangular aperture 2010 allows for efficient light transmission to the corners of photosensitive pixel array 262 while effectively blocking undesirable light entry into lens system 210 near the sides of planar surface 224.

Figure 21:
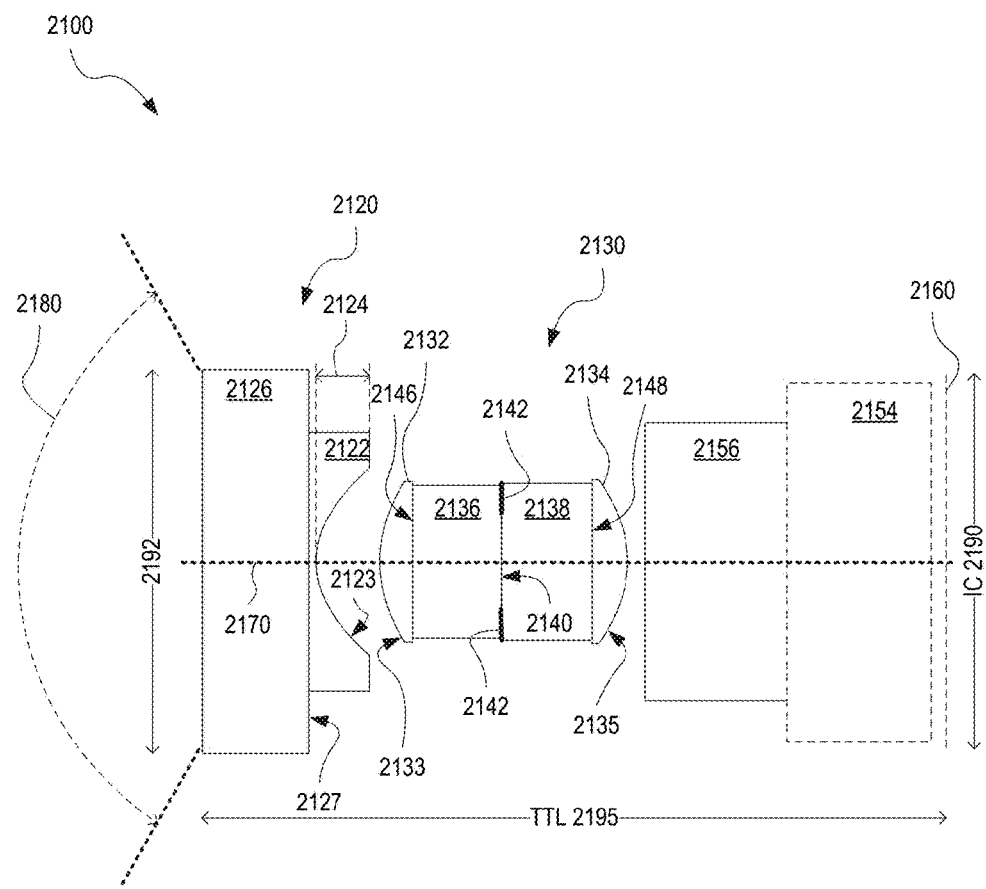
FIG. 21 illustrates the optical configuration of one exemplary ultra-small lens system with wide FOV.

FIG. 21 illustrates the optical configuration of one exemplary ultra-small lens system 2100 with wide FOV. Ultra-small lens system 2100 includes a one-sided wafer-level lens 2120 and a two-sided wafer-level lens 2130, optically coupled in series. While particular values of parameters for ultra-small lens system 2100 are disclosed in the following, actual values may deviate from the disclosed values. A disclosed parameter value is a particular example of a range of values and may be extended to such a range of values. Ultra-small lens system 2100 is an embodiment of lens system 510 including transparent substrate 472, and the optical configuration of ultra-small lens system 2100 may be implemented in ultra-small lens systems 510, 610, 810, and 1710. Wafer-level lenses 2120 and 2130 are embodiments of wafer-level lenses 220 and 230, respectively.

Ultra-small lens system 2100 is configured to image a scene onto an image plane 2160 with a cover glass 2154 placed between ultra-small lens system 2100 and image plane 2160. This cover glass is, for example, made of glass, plastic, or a combination thereof. Cover glass 2154 is an embodiment of cover glass 270, and substrate 2156 is an embodiment of transparent substrate 472. Ultra-small lens system 2100 has a total track length 2195 and forms an image circle 2190 on image plane 2160. Ultra-small lens system 2100 has a FOV characterized by FOV angle 2180. FIG. 21 further indicates the optical axis 2170 of ultra-small lens system 2100.

Wafer-level lens 2120 includes a substantially planar substrate 2126 and a lens element 2122 disposed on a substantially planar surface 2127 of substrate 2126. Surface 2127 faces image plane 2160. Lens element 2122 has an aspheric concave lens surface 2123 facing image plane 2160. Substrate 2126 and lens element 2122 are embodiments of substrate 226 and lens element 222, respectively.

Wafer-level lens 2130 includes two substantially planar substrates 2136 and 2138, a lens element 2132, and a lens element 2134. Substrates 2136 and 2138 are connected to each other at an interface 2140. In one example, substrates 2136 and 2138 are bonded to each other. Lens element 2132 is disposed on a substantially planar surface 2146 of substrate 2136. Surface 2146 faces away from image plane 2160. Lens element 2132 includes an aspheric convex lens surface 2133 facing away from image plane 2160. Lens element 2134 is disposed on a substantially planar surface 2148 of substrate 2138. Surface 2148 faces away from image plane 2160. Lens element 2134 includes an aspheric convex lens surface 2135 facing away from image plane 2160. Wafer-level lens 2130 includes a aperture stop 2142 located at interface 2140. Aperture stop 2142 is, for example, an opaque coating with an opening. Lens elements 2132 and 2134 are embodiments of lens elements 232 and 234 respectively. Substrates 2136 and 2138 are embodiments of substrates 532 and 534, respectively. Aperture stop 242 is an embodiment of stop aperture 536.

The use of two substrates (i.e., substrates 2136 and 2138) facilitates placement of aperture stop 2142 between lens elements 2132 and 2134 and at a distance from both of lens elements 2132 and 2134. In contrast, if only one substrate was used, aperture stop 2142 would need to be placed at an interface between this substrate and either lens element 2132 or lens element 2134. If only such substrate-to-lens element interfaces were available for placement of a aperture stop, the aperture stop would have to be either (a) be placed very asymmetrically and be much closer to one side of the wafer-level lens than the other side of the wafer-level lens or (b) one of the lens elements would need to be very thick to achieve a more symmetric placement of the aperture stop with the aperture stop relatively centrally located within the wafer-level lens. In ultra-small lens system 2100, this issue is overcome by using a composite substrate with two substrates, substrates 2136 and 2138, such that aperture stop 2142 may be placed at essentially any location within this composite substrate. In compact lens system 2100, aperture stop 2142 is relatively symmetrically placed between the side of wafer-level lens 2130 further from image plane 2160 and the side of wafer-level lens 2130 closer to image plane 2160 to preserve the symmetry of each ray bundle respectively associated with a field location.

Each of substrates 2136 and 2138 may have diameter greater than that shown in FIG. 21, without departing from the scope hereof.

Without departing from the scope hereof, the diameter of one or more of lens elements 2122, 2132, and 2134 and substrate 2126 may be greater than shown in FIG. 21, although the optical performance presented below assumes optically active areas as illustrated in FIG. 21.

In operation, substrate 2126 receives incident rays, which are subsequently collected by lens surface 2123. Lens surface 2133 adjusts the propagation direction of rays collected by lens surface 2123 and directs these rays through aperture stop 2142. Lens surface 2135 bends bundles of rays from the respective field locations to reach image plane 2160. Lens surface 2135 also balances aberrations introduced by optical elements of compact lens system 2100 upstream of lens surface 2135.

Tables 1A, 1B and 1C lists the lens data of ultra-small lens system 2100. The lens data includes values of design parameters for substrates 2126, 2136, and 2138, lens elements 2122, 2132, and 2134, lens surfaces 2123, 2133, and 2135, and aperture stop 2142. The lens data also includes the configuration of substrate 2156, cover glass (CG) 2154, and a gap between cover glass 2154 and image plane (IMA) 2160. FOV angle 2180 is 110 degrees, and Table 1A lists an assumed object (OBJ) location and diameter according to FOV angle 2180. Material properties and thicknesses of each of substrate 2126, lens element 2122, lens element 2132, substrate 2136, substrate 2138, lens element 2134, cover glass 2154, and substrate 2156 are indicated in Table 1A in the same row as the first surface of the respective element, as viewed from the object side. Material properties indicated in Table 1A are (a) the index of refraction $n_D$ at the Fraunhofer D-line $\lambda_D$=589.3, and (b) the Abbe number. The Abbe number is a measure of optical dispersion in a material and is defined as $V_d=(n_D-1)/(n_F-n_C)$, where $n_F$ and $n_C$ are the indices of refraction at the Fraunhofer F-line $\lambda_F$=486.1 nm and the Fraunhofer C-line $\lambda_C$=656.3 nm, respectively.

Tables 1B and 1C list the aspheric coefficients of each of lens surfaces 2123, 2133, and 2135. For each of these aspheric lens surfaces, the surface profile can be expressed as $$Z(s) = \frac{Cs^1}{1+\sqrt{1-(1+k)C^2s^2}} + A_4 s^4 + A_6 s^6 + \cdots,$$

where Z is the surface sag parallel to optical axis 2170 as a function of the radial distance s from optical axis 2170, C is the inverse of the radius of curvature, k is the conic constant, and $A_4, A_6, \ldots$ are the $4^{th}, 6^{th}, \ldots$ order aspheric terms.

Ultra-small lens system 2100 has a working F-number of 3.3, effective focal length EFFL of 0.451 mm, IC diameter 2190 of 1.06 mm, and TTL 295 of 2.10 mm. It follows that TTL/EFFL=4.66 for ultra-small lens system 2100.

As evident from Table 1A, lens element 2132 is of a material different from that of lens element 2134, while lens elements 2122 and 2134 have the same material properties in terms of index of refraction and Abbe number. The Abbe number of lens element 2132 is 31 while the Abbe number of each of lens elements 2122 and 2134 is 57. In one example, lens elements 2122, 2132, and 2134 are made from a polymer such as an epoxy. In an embodiment, ultra-small lens system 2100 is composed of reflow-compatible materials, such as materials that have identical, or substantially identical, optical properties before and after being heated to 260 degrees Celsius for 10 seconds.

Ultra-small lens system 2100 has maximum transverse extent 2192. Maximum transverse extent 2192 is defined by the diameter of substrate 2126, which is 1.09 mm. It is understood that, while the optical design is based on optical elements with cylinder symmetry (that is, circular cross section orthogonal to optical axis 2170), actual elements may be rectangular or square. For example, in one embodiment, substrate 2126 is square in the transverse dimensions as a result of dicing wafer-level lens 2120 from a wafer, such that maximum transverse extent 2192 is 1.54 mm, taken along the diagonal of the square, while the side length of the square is 1.09 mm. Sag height 2124 of lens surface 2123 is about 0.15 mm, and the diameter D1 of lens surface 2123 is 0.5325 mm, such that the ratio of D1 to sag height 2124 is about 3.6.

Lens surface 2123 has focal length F1, lens surface 2133 has focal length F2, and lens surface 2135 has focal length F3, such that 1.35<F2/EFFL<1.75 and −0.9<F1/F3<−0.7.

TABLE 1A

| Surface | Radius of curvature [mm] | Thickness [mm] | $n_D$ | $V_d$ | Diameter [mm] |
|---|---|---|---|---|---|
| OBJ | Infinity | 10.0000 | | | 33.7 |
| 2126 | Infinity | 0.3000 | 1.517 | 63 | 1.09 |
| 2122 | Infinity | 0.0200 | 1.511 | 57 | 0.7355 |
| 2123 | 0.2350 | 0.1814 | | | 0.5325 |
| 2132/2133 | 0.3740 | 0.0928 | 1.590 | 31 | 0.4570 |
| 2136 | Infinity | 0.2500 | 1.517 | 63 | 0.4351 |
| 2138/STO | Infinity | 0.2550 | 1.517 | 63 | 0.1920 |
| 2134 | Infinity | 0.1008 | 1.511 | 57 | 0.4469 |
| 2135 | −0.3227 | 0.0500 | | | 0.4667 |
| 2156 | Infinity | 0.4050 | 1.517 | 63 | 0.5766 |
| CG | Infinity | 0.4000 | 1.517 | 63 | 0.7903 |
| Gap | Infinity | 0.0450 | | | 1.0060 |
| IMA 2160 | Infinity | | | | 1.0600 |

TABLE 1B

| | Aspheric coefficient | | | |
|---|---|---|---|---|
| Surface | k | $A_4$ | $A_6$ | $A_8$ |
| 2123 | −0.6821 | 2.9977 | −322.1547 | 7864.9826 |
| 2133 | −0.5750 | 0.4280 | −183.8806 | 9016.2761 |
| 2135 | −1.0648 | −2.8303 | 554.7405 | −32309.0380 |

TABLE 1C

| | Aspheric coefficient | | |
|---|---|---|---|
| Surface | $A_{10}$ | $A_{12}$ | $A_{14}$ |
| 2123 | −96105.4530 | 434407.3700 | 0.0000 |
| 2133 | −193405.0000 | 1443867.6000 | 0.0000 |
| 2135 | 878282.3200 | −11133684.0000 | 53006285.0000 |

Figure 22:
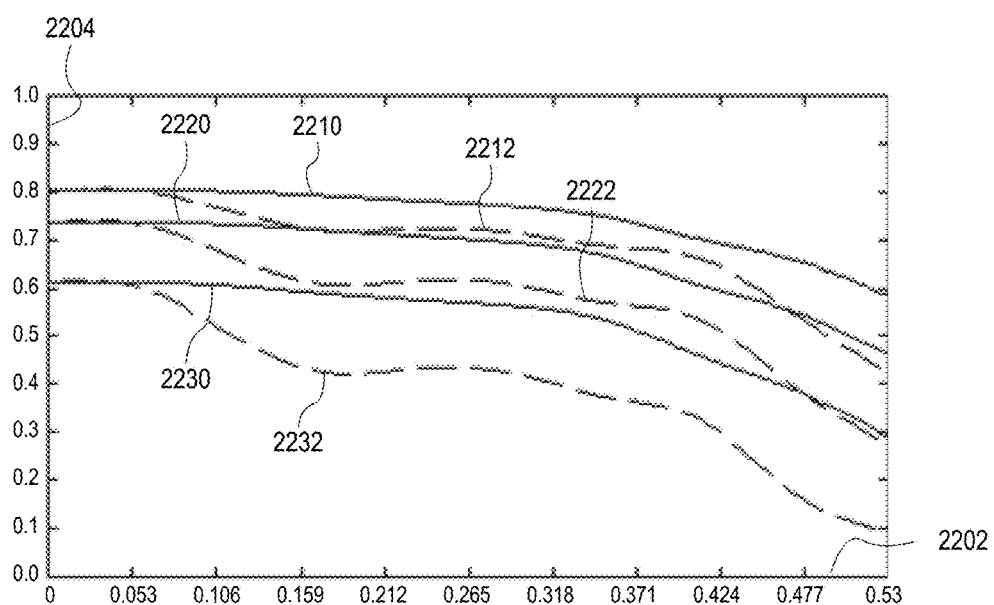
FIG. 22 shows the optical performance of the ultra-small lens system of FIG. 21.

FIG. 22 shows the optical performance of ultra-small lens system 2100 as evaluated by the Zemax® Optical Design Program. Specifically, FIG. 22 shows the modulus of the optical transfer function (MTF) 2204 versus Y field 2202 in millimeters. Curves 2210 and 2212 are the tangential and sagittal MTF, respectively, for a spatial frequency of 71 cycles/mm. Curves 2220 and 2222 are the tangential and sagittal MTF, respectively, for a spatial frequency of 95 cycles/mm. Curves 2230 and 2232 are the tangential and sagittal MTF, respectively, for a spatial frequency of 142 cycles/mm. FIG. 22 demonstrates excellent imaging performance for ultra-small lens system 2100 across the Y field.

Without departing from the scope hereof, each of lens systems 210, 410, 510, 610, 710, 810, and 1710 may be supplied as a stand-alone system configured to cooperate with an image sensor 250 supplied by a third party.

Combinations of Features

Features described above as well as those claimed below may be combined in various ways without departing from the scope hereof. For example, it will be appreciated that aspects of one ultra-small camera module with wide field of view, or associated lens system or method of manufacture, described herein may incorporate or swap features of another ultra-small camera module with wide field of view, or associated lens system or method of manufacture, described herein. The following examples illustrate some possible, non-limiting combinations of embodiments described above. It should be clear that many other changes and modifications may be made to the systems herein without departing from the spirit and scope of this invention:

(A1) An ultra-small camera module with a wide field of view may include (a) a wafer-level lens system for forming, on an image plane, an image of a wide field-of-view scene, wherein the wafer-level lens system includes (i) a distal planar surface positioned closest to the scene and no more than 2.5 millimeters away from the image plane in direction along optical axis of the wafer-level lens system, and (ii) a plurality of lens elements optically coupled in series along the optical axis, each of the lens elements having a curved surface, and (b) an image sensor mechanically coupled to the wafer-level lens system and including a rectangular array of photosensitive pixels, positioned at the image plane, for capturing the image, wherein the cross section of the ultra-small camera module, orthogonal to the optical axis, is rectangular with side lengths no greater than 1.5 millimeters.

(A2) In the ultra-small camera module denoted as (A1), the wafer-level lens system may further include an aperture disposed on the distal planar surface and configured to block light incident on the distal planar surface outside a central area that is shaped as a rounded rectangle, to minimize extent of the wafer-level lens system transverse to the optical axis while optimizing protection from stray light reaching the photosensitive pixels.

(A3) In the ultra-small camera module denoted as (A2), the rounded rectangle may have same aspect ratio as the cross section.

(A4) In any of the ultra-small camera modules denoted as (A1) through (A3), the image sensor may further include a cover glass, and the wafer-level lens system may further include a transparent substrate disposed on the cover glass to reduce angles, relative to the optical axis, of light from the scene, so as to reduce extent of image sensor transverse to the optical axis necessary to capture the image.

(A5) In the ultra-small camera module denoted as (A4), the transparent substrate may have thickness, along the optical axis, in range from 0.3 to 0.5 millimeters.

(A6) In either or both of the ultra-small camera modules denoted as (A4) and (A5), the transparent substrate may be bonded to the cover glass.

(A7) In any of the ultra-small camera modules denoted as (A4) through (A6), the wafer-level lens system may further include a wavelength filter coated onto side of the transparent substrate facing the scene.

(A8) In the ultra-small camera module denoted as (A7), the wafer-level lens system may further include (a) a wafer-level lens implementing at least one of the lens elements and (b) a spacer bonded to the wafer-level lens and side of the transparent substrate associated with the wavelength filter to couple the wafer-level lens to the image sensor.

(A9) In any of the ultra-small camera modules denoted as (A1) through (A8), the plurality of lens systems may include (a) a one-sided wafer-level lens including (i) a first substrate implementing the distal planar surface, and (ii) a first lens element disposed on side of the first substrate facing the image sensor, and a two-sided wafer-level lens disposed between the one-sided wafer-level lens and the image sensor and including (i) a second substrate, (ii) a second lens element disposed on side of the second substrate facing the one-sided wafer-level lens, and (iii) a third lens element disposed on side of the second substrate facing the image sensor.

(A10) In the ultra-small camera module denoted as (A9), the second substrate may be a composite substrate including a first sub-substrate coupled with the second lens element, a second sub-substrate coupled with the third lens element, and a stop aperture disposed at the interface between the first sub-substrate and the second sub-substrate.

(A11) In either or both of the ultra-small camera modules denoted as (A9) and (A10), the first lens element may include a concave lens surface, facing the image sensor, and a first planar surface surrounding the concave lens surface and facing the image sensor, and the second lens element may include a convex lens surface, facing away from the second substrate, and a second planar surface surrounding the convex lens surface and facing away from the image sensor, wherein the second planar surface is bonded to the first planar surface.

(A12) In the ultra-small camera module denoted as (A11), the second planar surface may be in direct contact with the first planar surface.

(A13) In either of both of the ultra-small camera modules denoted as (A11) and (A12), the image sensor may further include a cover glass, and the wafer-level lens system may further include a transparent substrate disposed on the cover glass to reduce angles, relative to the optical axis, of light from the scene, so as to reduce extent of image sensor transverse to the optical axis necessary to capture the image.

(A14) In the ultra-small camera module denoted as (A13), the wafer-level lens system may further include a wavelength filter coated onto side of the transparent substrate facing the scene, and a spacer bonded to the third lens element and side of the transparent substrate associated with the wavelength filter, to couple the wafer-level lens to the image sensor.

(A15) In the ultra-small camera module denoted as (A14), the second substrate may be a composite substrate include a first sub-substrate coupled with the second lens element, a second sub-substrate coupled with the third lens element, and a stop aperture disposed at interface between the first sub-substrate and the second sub-substrate.

(A16) In any of the ultra-small camera modules denoted as (A1) through (A15), the wafer-level lens system may further include an aperture disposed on the distal planar surface and configured to block light incident on the distal planar surface outside a central area that is shaped as a rounded rectangle, to optimize (a) protection from stray light reaching the photosensitive pixels and (b) proper transmission of light through the wafer-level lens system to the photosensitive pixels.

(A17) Any of the ultra-small camera modules denoted as (A1) through (A16) may have field-of-view angle of at least 110 degrees.

(B1) A wafer-level method for manufacturing an ultra-small camera module with wide field of view may include (a) molding a first lens layer onto a first substrate, wherein the first lens layer is composed of a first planar layer and a plurality of convex lens surfaces protruding from the first planar layer in direction away from the first substrate, (b) molding a second lens layer onto a second substrate, wherein the second lens layer is composed of a second planar layer and a plurality of recesses that form a respective plurality of concave lens surfaces recessed from the second planar layer, and (c) bonding the first planar layer directly to the second planar layer to form a composite wafer, such that optical axes of the convex lens surfaces are aligned with optical axes of the concave lens surfaces, respectively, with a gap between each of the convex lens surfaces and a corresponding one of the concave lens surfaces.

(B2) In the wafer-level method denoted as (B1), the step of bonding may include bonding the first planar layer to the second planar layer such that each of the convex lens surfaces protrudes into a corresponding one of the recesses.

(B3) In either or both of the wafer-level methods denoted as (B1) and (B2), the step of bonding may include bonding the first planar layer to the second planar layer such that distance from each of the convex lens surfaces to a corresponding one of the concave lens surfaces, along directions parallel to the optical axes, is no more than 200 microns.

(B4) In any of the wafer-level methods denoted as (B1) through (B3), in the step of molding a second lens layer, the diameter of the recesses may be greater than the diameter of the concave lens surfaces such that, in the step of bonding, the first planar layer is bonded to the second planar layer with a gap of at least 50 microns between the convex lens surfaces and the concave lens surfaces, respectively.

(B5) Any of the wafer-level methods denoted as (B1) through (B4), may further include molding a third lens layer onto side of the first substrate facing away from the first lens layer, wherein the third lens layer is composed of a third planar layer and a plurality of opposite facing convex lens surfaces protruding from the third planar layer in direction away from the first substrate.

(B6) The wafer-level method denoted as (B5) may further include bonding the third planar layer to a first side of a spacer wafer and bonding a second side of the spacer wafer to a glass substrate, wherein the first side and the second side face in opposite directions.

(B7) Any of the wafer-level methods denoted as (B1) through (B6) may further include coating an aperture layer onto the second substrate on side of second substrate facing away from the second lens layer, wherein the aperture layer forms a plurality of apertures aligned with the plurality of concave lens surfaces, and wherein each of the apertures is shaped as a rounded rectangle.

(C1) An ultra-small wafer-level lens system for imaging a wide field of view may include (a) a first substrate, (b) a first lens element disposed on the first substrate and including (i) a concave lens surface facing away from the first substrate and (ii) a first planar surface surrounding the concave lens surface and facing away from the first substrate, (b) a second substrate, and (c) a second lens element disposed on the second substrate and including (i) a convex lens surface facing away from the second substrate and (ii) a second planar surface surrounding the convex lens surface and facing away from the second substrate, wherein the second planar surface is bonded to the first planar surface.

(C2) In the ultra-small wafer-level lens denoted as (C1), the second planar surface may be bonded directly to the first planar surface such that the distance from the concave lens surface to the convex lens surface is fully determined by the geometry of the first lens element and the second lens element.

(C3) In either or both of the ultra-small wafer-level lens systems denoted as (C1) and (C2), the concave lens surface may be formed in a recess from the first planar surface, and the recess may have larger diameter than the concave lens surface to allow the convex lens surface to be positioned closer than the first planar surface to the first substrate while leaving a gap between the convex lens surface and the first lens element.

(C4) In the ultra-small wafer-level lens system denoted as (C3), the gap may be at least 50 microns.

(C5) In any of the ultra-small wafer-level lens systems denoted as (C1) through (C4), the distance from the concave lens surface to the convex lens surface along directions parallel to optical axis may be no more than 200 microns.

(C6) In any of the ultra-small wafer-level lens systems denoted as (C1) through (C5), the concave lens surface may have stronger curvature than the convex lens surface.

Changes may be made in the above modules, systems, and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present module, system, and method, which, as a matter of language, might be said to fall therebetween.

What is claimed is:

1. An ultra-small camera module with wide field of view, comprising:
    a wafer-level lens system for forming, on an image plane, an image of a wide field-of-view scene, the wafer-level lens system including
        (a) a distal planar surface positioned closest to the scene and no more than 2.5 millimeters away from the image plane in direction along optical axis of the wafer-level lens system, and
        (b) a plurality of lens elements optically coupled in series along the optical axis, each of the lens elements having a curved surface; and
    an image sensor mechanically coupled to the wafer-level lens system and including a rectangular array of photosensitive pixels, positioned at the image plane, for capturing the image;
    wherein cross section of the ultra-small camera module, orthogonal to the optical axis, is rectangular with side lengths no greater than 1.5 millimeters; and
    wherein the plurality of lens elements comprise:
        a one-sided wafer-level lens including:
            (i) a first substrate implementing the distal planar surface, and
            (ii) a first lens element disposed on side of the first substrate facing the image sensor, and
        a two-sided wafer-level lens disposed between the one-sided wafer-level lens and the image sensor and including:
            (i) a second substrate,
            (ii) a second lens element disposed on side of the second substrate facing the one-sided wafer-level lens, and
            (iii) a third lens element disposed on side of the second substrate facing the image sensor.

2. The ultra-small camera module of claim 1, the wafer-level lens system further comprising an aperture disposed on the distal planar surface and configured to block light incident on the distal planar surface outside a central area that is shaped as a rounded rectangle.

3. The ultra-small camera module of claim 2, the rounded rectangle having same aspect ratio as the cross section.

4. The ultra-small camera module of claim 1,
    the image sensor further comprising a cover glass; and
    the wafer-level lens system further comprising a transparent substrate disposed on the cover glass to reduce angles, relative to the optical axis, of light from the scene, to reduce extent of image sensor transverse to the optical axis necessary to capture the image.

5. The ultra-small camera module of claim 4, the transparent substrate having thickness, along the optical axis, in range from 0.3 to 0.5 millimeters.

6. The ultra-small camera module of claim 4, the transparent substrate being bonded to the cover glass.

7. The ultra-small camera module of claim 4, the wafer-level lens system further comprising a wavelength filter coated onto side of the transparent substrate facing the scene.

8. The ultra-small camera module of claim 7, the wafer-level lens system further comprising:
   a wafer-level lens implementing at least one of the lens elements; and
   a spacer bonded to the wafer-level lens and side of the transparent substrate associated with the wavelength filter, to couple the wafer-level lens to the image sensor.

9. The ultra-small camera module of claim 1, the second substrate being a composite substrate comprising:
   a first sub-substrate coupled with the second lens element;
   a second sub-substrate coupled with the third lens element; and
   a stop aperture disposed at interface between the first sub-substrate and the second sub-substrate.

10. The ultra-small camera module of claim 1,
   the first lens element including a concave lens surface, facing the image sensor, and a first planar surface surrounding the concave lens surface and facing the image sensor; and
   the second lens element including a convex lens surface, facing away from the second substrate, and a second planar surface surrounding the convex lens surface and facing away from the image sensor, the second planar surface being bonded to the first planar surface.

11. The ultra-small camera module of claim 10, the second planar surface being in direct contact with the first planar surface.

12. The ultra-small camera module of claim 10,
   the image sensor further comprising a cover glass; and
   the wafer-level lens system further comprising a transparent substrate disposed on the cover glass to reduce angles, relative to the optical axis, of light from the scene, to reduce extent of image sensor transverse to the optical axis necessary to capture the image.

13. The ultra-small camera module of claim 12, the wafer-level lens system further comprising:
   a wavelength filter coated onto side of the transparent substrate facing the scene; and
   a spacer bonded to the third lens element and side of the transparent substrate associated with the wavelength filter, to couple the wafer-level lens to the image sensor.

14. The ultra-small camera module of claim 13, the second substrate being a composite substrate comprising:
   a first sub-substrate coupled with the second lens element;
   a second sub-substrate coupled with the third lens element; and
   a stop aperture disposed at interface between the first sub-substrate and the second sub-substrate.

15. The ultra-small camera module of claim 1, the wafer-level lens system further comprising an aperture disposed on the distal planar surface and configured to block light incident on the distal planar surface outside a central area that is shaped as a rounded rectangle, to optimize (a) protection from stray light reaching the photosensitive pixels and (b) proper transmission of light through the wafer-level lens system to the photosensitive pixels.

16. The ultra-small camera module of claim 1, having field-of-view angle of at least 110 degrees.

* * * * *